(12) United States Patent
Piskun et al.

(10) Patent No.: US 9,011,317 B2
(45) Date of Patent: Apr. 21, 2015

(54) GENTLE HEMORRHOID TREATMENT OFFERING A SUBSTANTIALLY PAINLESS HEALING

(71) Applicants: Gregory Piskun, Morganville, NJ (US); Patrick Gutelius, Monroe, CT (US); Oleg Shikhman, Trumbull, CT (US)

(72) Inventors: Gregory Piskun, Morganville, NJ (US); Patrick Gutelius, Monroe, CT (US); Oleg Shikhman, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/106,600

(22) Filed: Dec. 13, 2013

(65) Prior Publication Data

US 2014/0128670 A1   May 8, 2014

Related U.S. Application Data

(60) Division of application No. 13/282,439, filed on Oct. 26, 2011, now Pat. No. 8,632,458, and a continuation-in-part of application No. 13/094,173, filed on Apr. 26, 2011, now Pat. No. 8,968,275.

(60) Provisional application No. 61/328,005, filed on Apr. 26, 2010.

(51) Int. Cl.

| *A61B 1/00* | (2006.01) |
|---|---|
| *A61B 17/30* | (2006.01) |
| *A61B 17/12* | (2006.01) |
| *A61B 1/31* | (2006.01) |
| *A61B 17/00* | (2006.01) |
| A61B 18/04 | (2006.01) |
| A61B 17/34 | (2006.01) |
| A61B 18/14 | (2006.01) |
| A61B 18/00 | (2006.01) |

(52) U.S. Cl.
CPC ............... *A61B 17/30* (2013.01); *A61B 18/04* (2013.01); *A61B 17/12013* (2013.01); *A61B 2017/3452* (2013.01); *A61B 2218/007* (2013.01); *A61B 18/1442* (2013.01); *A61B 18/1485* (2013.01); *A61B 2018/005* (2013.01); *A61B 2018/00589* (2013.01); *A61B 1/31* (2013.01); *A61B 17/00234* (2013.01)

(58) Field of Classification Search
USPC ............... 600/105, 114; 606/32–50, 205–208
See application file for complete search history.

(56) References Cited

U.S. PATENT DOCUMENTS

| 457,787 A | 8/1891 | Leisenring |
|---|---|---|
| 2,482,971 A | 9/1949 | Golson |
| 3,382,873 A | 5/1968 | Banich et al. |
| 3,760,810 A | 9/1973 | Van Hoorn |

(Continued)

FOREIGN PATENT DOCUMENTS

| EP | 0736285 | 10/1996 |
|---|---|---|
| GB | 2365340 | 2/2002 |

(Continued)

OTHER PUBLICATIONS

PCT/US2006/030464 International Search Report (Jun. 20, 2007).

(Continued)

*Primary Examiner* — Matthew J Kasztejna

(57) ABSTRACT

The teachings provided herein are directed to a methods and devices for treating a hemorrhoid in a subject in a manner that produces substantially less post-procedural pain in the subject, the method minimizing or avoiding a removing or a necrosis of a rectal tissue fold.

22 Claims, 8 Drawing Sheets

(56) References Cited

U.S. PATENT DOCUMENTS

| | | |
|---|---|---|
| 4,257,419 A | 3/1981 | Goltner et al. |
| 5,318,589 A | 6/1994 | Lichtman |
| 5,402,772 A | 4/1995 | Moll et al. |
| 5,411,508 A | 5/1995 | Bessler et al. |
| 5,443,472 A | 8/1995 | Li |
| 5,570,692 A | 11/1996 | Morinaga |
| 5,655,698 A | 8/1997 | Yoon |
| 5,665,062 A | 9/1997 | Houser |
| 5,716,321 A | 2/1998 | Kerin et al. |
| 5,873,815 A | 2/1999 | Kerin et al. |
| 5,876,369 A | 3/1999 | Houser |
| 5,935,056 A | 8/1999 | Kering et al. |
| 5,947,983 A | 9/1999 | Solar et al. |
| 5,968,033 A | 10/1999 | Fuller et al. |
| 6,019,733 A | 2/2000 | Farascioni |
| 6,032,673 A | 3/2000 | Savage et al. |
| 6,102,271 A | 8/2000 | Longo et al. |
| 6,119,913 A | 9/2000 | Adams et al. |
| 6,126,594 A | 10/2000 | Bayer |
| 6,142,931 A | 11/2000 | Kaji |
| 6,142,933 A | 11/2000 | Longo et al. |
| 6,179,832 B1 | 1/2001 | Jones et al. |
| 6,196,966 B1 | 3/2001 | Kerin et al. |
| 6,214,024 B1 | 4/2001 | Houser |
| 6,264,086 B1 | 7/2001 | McGuckin, Jr. |
| 6,277,065 B1 | 8/2001 | Donofrio |
| 6,277,066 B1 | 8/2001 | Irwin |
| 6,302,311 B1 | 10/2001 | Adams et al. |
| 6,343,731 B1 | 2/2002 | Adams et al. |
| 6,398,795 B1 | 6/2002 | McAlister et al. |
| 6,428,473 B1 | 8/2002 | Leonard et al. |
| 6,478,210 B2 | 11/2002 | Adams et al. |
| 6,494,881 B1 | 12/2002 | Bales et al. |
| 6,540,761 B2 | 4/2003 | Houser |
| 6,575,978 B2 | 6/2003 | Peterson et al. |
| 6,595,917 B2 | 7/2003 | Nieto |
| 6,616,603 B1 | 9/2003 | Fontana |
| 6,695,198 B2 | 2/2004 | Adams et al. |
| 6,716,222 B2 | 4/2004 | McAlister et al. |
| 6,805,273 B2 | 10/2004 | Bilotti et al. |
| 6,808,491 B2 | 10/2004 | Kortenbach et al. |
| 6,840,423 B2 | 1/2005 | Adams et al. |
| 6,866,178 B2 | 3/2005 | Adams et al. |
| 6,872,204 B2 | 3/2005 | Houser |
| 6,874,669 B2 | 4/2005 | Adams et al. |
| 6,923,806 B2 | 8/2005 | Hooven et al. |
| 6,938,814 B2 | 9/2005 | Sharma et al. |
| 6,979,290 B2 | 12/2005 | Mourlas et al. |
| 7,014,646 B2 | 3/2006 | Adams |
| 7,029,438 B2 | 4/2006 | Morin et al. |
| 7,059,331 B2 | 6/2006 | Adams et al. |
| 7,118,528 B1 | 10/2006 | Piskun |
| 7,169,115 B2 | 1/2007 | Nobis et al. |
| 7,334,718 B2 | 2/2008 | McAlister et al. |
| 7,452,329 B2 | 11/2008 | Bastia et al. |
| 7,534,204 B2 | 5/2009 | Starksen et al. |
| 7,546,939 B2 | 6/2009 | Adams et al. |
| 7,717,861 B2 | 5/2010 | Weikel et al. |
| 7,882,995 B2 | 2/2011 | McAlister et al. |
| 7,972,299 B2 | 7/2011 | Carter et al. |
| 8,002,795 B2 | 8/2011 | Beetel |
| 8,016,748 B2 | 9/2011 | Mourlas et al. |
| 8,100,822 B2 | 1/2012 | Piskun et al. |
| 2002/0111639 A1 | 8/2002 | Armstrong |
| 2002/0173786 A1 | 11/2002 | Kortenbach et al. |
| 2004/0002706 A1 | 1/2004 | Houser |
| 2004/0033202 A1 | 2/2004 | Cooper et al. |
| 2004/0158263 A1 | 8/2004 | McAlister et al. |
| 2005/0119523 A1 | 6/2005 | Starksen et al. |
| 2005/0277975 A1 | 12/2005 | Saadat et al. |
| 2006/0049231 A1 | 3/2006 | Leiboff et al. |
| 2006/0191975 A1 | 8/2006 | Adams et al. |
| 2006/0200040 A1 | 9/2006 | Weikel, Jr. et al. |
| 2006/0264706 A1 | 11/2006 | Piskun |
| 2007/0255207 A1 | 11/2007 | Hangai et al. |
| 2008/0083813 A1 | 4/2008 | Zemlok et al. |
| 2008/0103498 A1 | 5/2008 | West et al. |
| 2008/0132835 A1 | 6/2008 | Nagamatsu et al. |
| 2008/0262511 A1 | 10/2008 | Delaney |
| 2008/0277448 A1 | 11/2008 | Roby et al. |
| 2009/0025910 A1 | 1/2009 | Hoffman et al. |
| 2009/0030369 A1 | 1/2009 | Nagamatsu et al. |
| 2009/0182332 A1 | 7/2009 | Long et al. |
| 2009/0182350 A1 | 7/2009 | McGown |
| 2009/0187074 A1 | 7/2009 | Saadat et al. |
| 2009/0259110 A1 | 10/2009 | Bastia et al. |
| 2009/0318940 A1 | 12/2009 | Piskun et al. |
| 2010/0010296 A1 | 1/2010 | Piskun et al. |
| 2010/0010297 A1 | 1/2010 | Piskun et al. |
| 2010/0023023 A1 | 1/2010 | Popovic et al. |
| 2010/0056870 A1 | 3/2010 | Piskun et al. |
| 2011/0224494 A1 | 9/2011 | Piskun et al. |
| 2011/0288538 A1 | 11/2011 | Piskun et al. |
| 2012/0059394 A1 | 3/2012 | Brenner et al. |
| 2013/0053833 A1 | 2/2013 | Doyle |

FOREIGN PATENT DOCUMENTS

| | | |
|---|---|---|
| WO | WO 97/13451 | 4/1997 |
| WO | WO 2004/004555 | 1/2004 |
| WO | WO 2007/017854 | 2/2007 |
| WO | WO 2007/019321 | 2/2007 |
| WO | WO 2007/032776 | 3/2007 |
| WO | WO 2011/041578 | 4/2011 |
| WO | WO 2011/084616 | 7/2011 |

OTHER PUBLICATIONS

PCT/US2006/030464 International Preliminary Report on Patentability (Feb. 5, 2008).
PCT/US2010/060802 International Search Report (Nov. 17, 2011).
PCT/US2010/060802 International Preliminary Report on Patentability (Jun. 19, 2012).
Notice of Reasons for Rejection for Japan Appl. No. 2008-525229 (Aug. 10, 2011).
PCT/US2010/050955 International Search Report (Jun. 23, 2011).
PCT/US06/30464 Written Opinion dated Jun. 20, 2007 and International Search Report.
European Search Report dated May 3, 2011 for European Patent Application No. 06789411.3.
Chinese Appl. No. 200680028706.2 English text of First Office Action (Jun. 20, 2007), Second Office Action (Feb. 5, 2010) and Third Office Action (Nov. 4, 2010).

GENTLE HEMORRHOID TREATMENT OFFERING A SUBSTANTIALLY PAINLESS HEALING

This application is a divisional of application Ser. No. 13/282,439 filed on Oct. 26, 2011, and is a continuation-in-part of application Ser. No. 13/094,173, filed on Apr. 26, 2011, which claims priority from Provisional application No. 61/328,005, filed Apr. 26, 2010. The entire contents of each of these applications are incorporated herein by reference.

BACKGROUND

1. Field of the Invention

The teachings provided herein are directed to methods and devices for gently treating a hemorrhoid in a subject in manner that produces substantially less post-procedural pain in the subject, the method avoiding a removing or a necrosis of a rectal tissue fold.

2. Description of the Related Art

Hemorrhoids present a worldwide problem that needs a gentle, yet effective, treatment with substantially less post-procedural pain. Moreover, those of skill in the art would appreciate having less complex and less expensive equipment for administering the treatment. Bleeding from hemorrhoids is the most common cause of rectal bleeding, which may cause anemia or be responsible for the person's substantially decreased quality of life. Prolapsed hemorrhoids, in particular, can create a quite serious discomfort to a patient, and the situation can get worse as the patient avoids the painful state-of-the-art treatments. As the patient avoids treatment, for example, a hemorrhoidal tissue can become redundant and/or suspensory ligaments can weaken. The hemorrhoid and/or lower rectal tissue folds, mucosal and submucosal, can then prolapse outside the rectum and cause bleeding and pain to the patient. The tissue, in effect, starts to become prone for prolapse; mobile from its original, healthy position in the patient; and move in and out of the anus creating inflammation, discomfort, pain, bleeding, infection, and the like. When further left untreated, the prolapse becomes more frequent and more prominent. Finally, hemorrhoids would become constantly prolapsed or would prolapse with a minor strain only, for example, during light coughing, sneezing, or even after walking or standing for a few minutes.

Current, state-of-the-art treatments are typically not gentle but, rather, are cumbersome for the physician and painful to the patient. The most popular methods generally call for use by a colorectal surgeon, in addition to an assistant. And, such methods often require the use of the expensive and demanding-in-use, multi-component instruments. Another group of the instruments for gastroenterologists requires costly and complex endoscope equipment, such as a power source, an optical fiber arrangement and camera system, and a computer processor. These treatments are associated with significant tissue trauma and, for example, can be designed to include tissue banding, cutting and/or stapling devices that lead to the removal, and/or intentional necrosis of rectal tissue, resulting in a substantial post-procedural pain.

Accordingly, one of skill will appreciate having a method of treating a hemorrhoid, or other such anorectal lesion, that (i) is simple, easy to learn, less cumbersome, and more cost-effective than current, state-of-art methods, in that it does not require the use of the more complex, cumbersome, and expensive systems; (ii) can be used without an assistant; (iii) can be readily learned and used by a gastroenterologist, or another non-surgical specialist, rather than being suited moreso for a colorectal surgeon with specialized training; (iv) is gentle for at least the reason that it does not require cutting, banding, and/or stapling for the removal, and/or intentional necrosis of, rectal tissue; (v) gently secures the rectal tissue with a controlled or limited pressure and for a limited time to avoid tissue damage during the occluding of a vascular supply to a hemorrhoid; and, as a result, (vi) facilitates an ischemic regression of a hemorrhoid with substantially less post procedural pain than the current procedures which are directed to a traumatic removal or necrosis of the rectal tissue. Those skilled in the art, and also the patients receiving hemorrhoid treatments, will appreciate having such a simple and cost-effective method of gently obtaining (vii) a loss of bulk and weight in the hemorrhoid without the unnecessary trauma and increased post-procedural pain in the patient that is now commonplace in the art.

SUMMARY

The teachings provided herein are directed to methods and devices for treating a hemorrhoid in a subject in a manner that produces substantially less post-procedural pain in the subject, the method avoiding a removing or a necrosis of a rectal tissue.

The teachings include a method of treating a hemorrhoid while minimizing tissue damage and substantially reducing post-procedural pain. Generally speaking, the method includes identifying a rectal tissue that comprises a vascular supply to a hemorrhoid, folding the rectal tissue to create a fold, securing the fold, and occluding the vascular supply to the hemorrhoid to facilitate an ischemic regression of the hemorrhoid, wherein the folding, securing, and occluding are all done gently to avoid a removal and/or a necrosis of the rectal tissue. The method can include inserting a therapeutic anoscope into an anus of a subject having the hemorrhoid, the anoscope operable to (i) form a fold in a rectal tissue orally to the hemorrhoid and above a dentate line in the subject; (ii) gently secure the fold; (iii) create a work space above the dentate line; and, (iv) provide a visualization of the rectal tissue without an image transmission through optic fibers.

The method can include gently securing the fold in the rectal tissue using a limited pressure to avoid a removal or a necrosis of the rectal tissue, the fold having the vascular supply for the hemorrhoid. Finally, the method can include occluding the vascular supply to the hemorrhoid in a targeted manner to otherwise minimize damage to the rectal tissue, the occluding including a component selected from the group consisting of heat, energy, or ligation. In addition to the other benefits set-forth herein, the gentle methods provided by the teachings can result in substantially less post-operative pain than a method of treating hemorrhoids that does not avoid the removal or the necrosis of the rectal tissue. The terms "minimize," "minimizing," "minimized," "avoid," "avoiding," "avoided," can be used interchangeably in some embodiments. Tissue damage can be minimized or avoided, for example, where a procedure is directed to reducing an amount of any unnecessary tissue damage that may otherwise be associated with a procedure. The gentle procedures taught herein, for example, are directed to preserving tissue during a hemorrhoid treatment by avoiding or minimizing the removal or the necrosis of the rectal tissue fold from the gentle procedures that lead to the tissue-preserving ischemic regressions of hemorrhoidal tissue.

It should be appreciated that the methods can be used to treat most any condition that could benefit from an ischemic regression of a hemorrhoid. For example, the methods can further comprise preventing, inhibiting, reducing, or eliminating a prolapse of the hemorrhoid.

The anoscope used in the methods can comprise a cylindrical, or substantially cylindrical, body for insertion into the subject, the cylindrical body creating a work space having a sufficient volume to perform the occluding of the vascular supply to the hemorrhoid. In such embodiments, the cylindrical, or substantially cylindrical, body comprises a side window and a convex surface that promotes an entry of the rectal tissue into the window for the gently securing of the rectal tissue.

The methods can include the use of a limited pressure on the rectal tissue for the gently securing of the fold, such that the tissue damage is minimized or avoided, prevented, or substantially prevented. In some embodiments, the limited pressure can range from, for example, about 50 kPa to about 500 kPa. Any system known to one of skill in the art can be used to control the amount of pressure applied to the tissue. For example, in some embodiments, the limited pressure can be obtained from the use of a spring-regulated pressure that facilitates the gently securing of the fold.

The methods can include occluding the vascular supply to the hemorrhoid in a targeted manner to avoid unnecessary tissue damage. In some embodiments, the targeted manner includes gently securing the fold into a constant tissue fold configuration for a suturing to selectively ligate the vascular supply during the occluding while otherwise avoiding the removal or the necrosis of the rectal tissue.

The occluding can be achieved using any method known to one of skill, to the extent that the method is gentle enough to avoid trauma to the patient in a manner consistent with the teachings herein. The occluding, for example, can include a selective and focused application of heat, energy, or ligation to the vascular supply to the hemorrhoid, the application limited to occluding the vascular supply while otherwise minimizing damage to the tissue. As such, the method can be applied in a targeted manner to minimized trauma to the patient. In some embodiments, the targeted manner can include heating at a temperature of about 50° C. to about 65° C. for an effective time to selectively coagulate the vascular supply during the occluding while avoiding the removal or the necrosis of the rectal tissue fold. In some embodiments, the targeted manner includes heating at a temperature of about 50° C. to about 65° C. for an effective time, the heating including applying an energy from a plurality of discrete regions on the pinching surfaces to a corresponding plurality of discrete areas on the fold to selectively coagulate the vascular supply during the occluding while preserving the remainder of the fold to avoid the removal or the necrosis of the rectal tissue fold.

The methods can include gently securing a fold of rectal tissue comprising the vascular supply to the hemorrhoid, and the gently securing can include any method known to one of skill that is gentle enough to avoid unnecessary trauma to the patient in a manner consistent with the teachings herein. The gentle securing can be used to create a constant tissue fold configuration to facilitate the occluding of the vascular supply to the hemorrhoid. The teachings provided herein include a means for securing the fold with a controlled pressure to provide the constant tissue fold configuration.

The controlled pressure can come from any configuration or orientation that gently secures the fold. In some embodiments, the body of the anoscope has a central axis, and the controlled pressure is applied at an angle ranging from about 0 degrees to about 90 degrees from the central axis. In some embodiments, the orientation in which the controlled pressure is applied can be adjusted in the anoscope. In some embodiments, the adjusting of the orientation can be done outside of the patient's body and, in some embodiments, after insertion of the anoscope into the patient's body.

The teachings are also directed to the therapeutic anoscopes. In some embodiments, the anoscope for treating a hemorrhoid in a subject can be designed to avoid trauma associated with removing a rectal tissue. The anoscope can include a cylindrical, or substantially cylindrical, anoscope body having a lumen, a proximal opening, a distal end configured for a first point of entry into an anus of a subject, and a side window having a shutter and pinching surfaces to form a fold in a rectal tissue orally to a hemorrhoid. The pinching surfaces can be configured to gently secure the fold with a limited pressure above a dentate line in a subject. The anoscope body can have any configuration that will support a mechanism that will operably function with the methods taught herein. In some embodiments, the anoscope body can be configured for providing a length sufficient to position the pinching surfaces above the dentate line in the subject. And, in some embodiments, the anoscope body can be configured for providing a volume in the lumen sufficient for receiving the fold of the rectal tissue for the occluding of the vascular supply to the hemorrhoid. In some embodiments, the shutter can be configured for opening the window to allow the rectal tissue to enter the window during the treatment of the hemorrhoid in the subject; creating the fold in the rectal tissue orally to the hemorrhoid; and, gently securing the fold with the limited pressure above the dentate line to avoid the removal or the necrosis of the rectal tissue that creates the trauma to the subject. The anoscope can be configured to (i) provide a visualization of the rectal tissue without an image transmission through optic fibers and (ii) facilitate an ischemic regression of the hemorrhoid through the occluding to treat the hemorrhoid in a manner that provides substantially less post procedural pain to the subject than a hemorrhoid treatment procedure that does not avoid the removal or the necrosis of the rectal tissue.

In some embodiments, the anoscope includes a means for securing the fold with a controlled pressure to provide a constant tissue fold configuration, the means including the structures taught herein, and variations that have substantially the same structure, that perform the gentle securing of tissue that is taught herein. In some embodiments, the anoscopes gently secure the tissues using limited pressure ranging from about 50 kPa to about 1000 kPa.

In some embodiments, the volume is sufficient for a suturing to selectively ligate the vascular supply during the occluding while otherwise avoiding the removal or the necrosis of the rectal tissue. And, in some embodiments, the volume is sufficient for an application of heat at a temperature of about 50° C. to about 65° C. for an effective time to selectively coagulate the vascular supply during the occluding while avoiding a necorsis of the rectal tissue fold. Moreover, in some embodiments, the volume is sufficient for an application of an RF energy to selectively coagulate the vascular supply during the occluding while avoiding a necrosis of the rectal tissue fold. In some embodiments, the RF energy or heat can be applied such that the temperature is ramped at a desired rate and heated for an effective amount of time to occlude the vascular supply to the hemorrhoid while otherwise minimizing damage to tissue surrounding the vascular supply.

In some embodiments, the anoscope body has a central axis, and the limited pressure is applied in the same, or substantially same, plane as a plane formed by the rectal tissue fold before the pinching, and at an angle ranging from about 0 degrees to about 90 degrees from the central axis. And, in some embodiments, the anoscope body can be at least partially translucent or transparent to facilitate viewing of a tissue, for example.

In some embodiments, a therapeutic anoscope is presented for treating a prolapsed hemorrhoid in a subject in a manner that creates substantially less post-procedural pain. The anoscope can have a cylindrical, or substantially cylindrical, anoscope body having a lumen, a proximal opening, a distal end configured for a first point of entry into an anus of a subject. The body can also include a side window having a shutter and pinching surfaces to form a fold in a rectal tissue orally to a prolapsed hemorrhoid and gently secure the fold with a limited pressure above a dentate line in a subject. The anoscope body can be configured for providing a length sufficient to position the pinching surfaces above the dentate line in the subject; and, providing a volume in the lumen sufficient for receiving the fold of the rectal tissue for an occluding of a vascular supply to the hemorrhoid. The shutter can be configured for opening the window to allow the rectal tissue to enter the window during a treatment of a hemorrhoid in the subject; creating the fold in the rectal tissue orally to the prolapsed hemorrhoid; and, gently securing the fold with a limited pressure ranging from about 50 kPa to about 1000 kPa above the dentate line to avoid a removal or a necrosis of the rectal tissue that creates a significant trauma to the subject. It should be appreciated that, in some embodiments, the rectal tissue can incorporate at least a portion of a hemorrhoid in a rectal tissue fold where, in some embodiments, the entire hemorrhoid may be incorporated. And, the anoscope can function to (i) directly visualize the rectal tissue without an endoscope having optic fibers and (ii) facilitate an ischemic regression of the prolapsed hemorrhoid through the occluding. The anoscopes taught herein can be used to treat the hemorrhoid in a manner that provides substantially less post procedural pain to the subject than a procedure that does not avoid the removal or the necrosis of the rectal tissue that creates trauma to the subject, facilitating the ischemic regression that results in a loss of bulk and weight in the prolapsed hemorrhoid.

It should be appreciated that the pinching surfaces that gently secure the tissue can have any configuration known to one of skill to accomplish the act of gently securing, for example, the fold of tissue for the occluding of the vascular supply to the hemorrhoid. The configuration should provide a securing surface and pressure that is gentle enough to avoid or minimize trauma to the patient in a manner consistent with the teachings herein. In some embodiments, the pinching surfaces can have an arcuate shape to facilitate a recruiting of the rectal tissue into the lumen of the body of the anoscope. And, in some embodiments, the pinching surfaces have a plurality of discrete regions on the pinching surfaces corresponding to a plurality of discrete areas on the fold to selectively coagulate the vascular supply during the occluding while preserving the remainder of the fold to avoid the removal or the necrosis of the rectal tissue.

The teachings are directed to a system for treating a hemorrhoid in a subject in a manner that creates substantially less post-procedural pain. In some embodiments, the system comprises a therapeutic anoscope as taught herein; and, an occlusion device operable for a targeted application of heat, energy, or ligation to the vascular supply to the hemorrhoid, the targeted application otherwise avoiding damage to the rectal tissue. In some embodiments, the occlusion device applies RF energy to the vascular supply to the hemorrhoid. In some embodiments, the occlusion device facilitates an application of a suture to the vascular supply to the hemorrhoid. And, in some embodiments, the occlusion device applies heat to the vascular supply to the hemorrhoid at a temperature ranging from about 50° C. to about 65° C. for an effective time to selectively coagulate the vascular supply during the occluding while avoiding a necrosis of the rectal tissue fold.

DETAILED DESCRIPTION OF THE INVENTION

The teachings provided herein are directed to methods and devices for treating a hemorrhoid in a subject in a manner that produces substantially less post-procedural pain in the subject, the method avoiding a removing or a necrosis of a rectal tissue.

Figure 1:
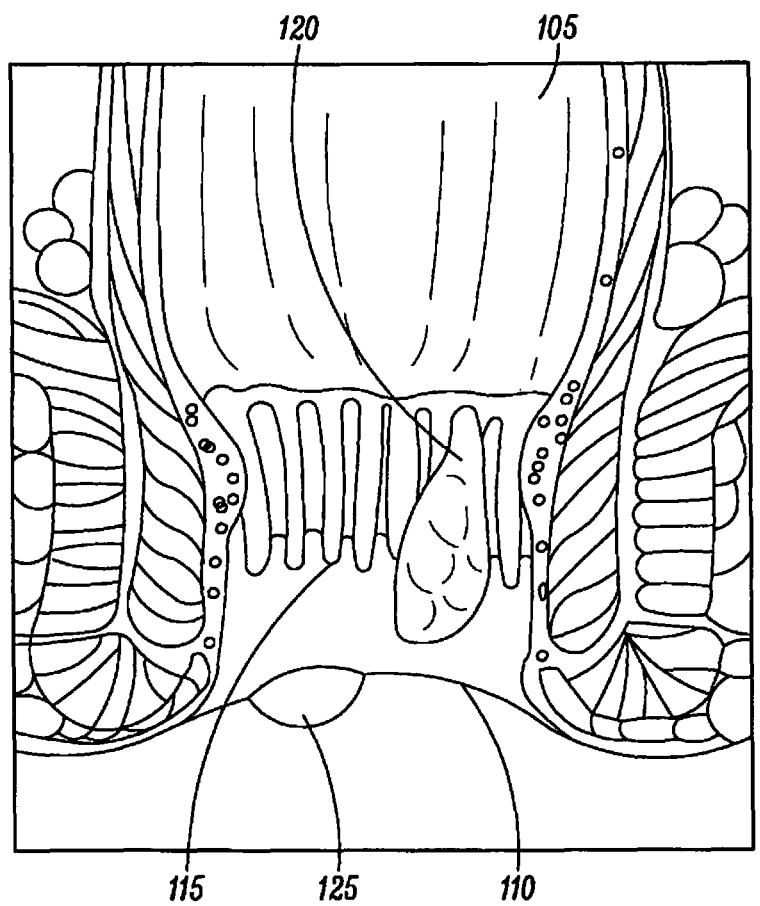
FIG. 1 illustrates an anus and rectum of a subject having an internal hemorrhoid and an external hemorrhoid, according to some embodiments.

FIG. 1 illustrates an anus and rectum of a subject having an internal hemorrhoid and an external hemorrhoid, according to some embodiments. The rectum 105 and anus 110 are separated by a dentate line 115. The internal hemorrhoid 120 is enlarged and is located below the dentate line 115, and external hemorrhoid 125 is located exterior to the anus 110. Both the internal hemorrhoid 120 and the external hemorrhoid 125 are masses of vascular tissue that can bleed, itch, and be painful to the subject. Hemorrhoids can be classed as "early" or "advanced," where the early hemorrhoids further classed as "grade I" or "grade II" hemorrhoids, and the advanced hemorrhoids are further classed as "grade III" or "grade IV" hemorrhoids. Grade I hemorrhoids bleed but do not prolapse outside the anal canal. Grade II hemorrhoids can suffer a mild prolapse and retract spontaneously. Grade III hemorrhoids can prolapse and require manual replacement into the anal canal. Grade IV hemorrhoids can be prolapsed tissue that can no longer be manually replaced. As tissue becomes redundant and/or suspensory ligaments weaken, the hemorrhoid and/or lower rectal tissues, whether mucosal or submucosal, can prolapsed outside the rectum causing bleeding, pain, and discomfort. There are about 13.2 million people with symptomatic hemorrhoids in the US only, and over 1 million new cases are diagnosed annually.

It should be appreciated by one of skill that the teachings set-forth herein can also be useful, in some embodiments, in the treatment of other superficial lesions, lesions other than hemorrhoids in some embodiments. Such lesions can include, but are not limited to rectal mucosal polyps, warts, and radiation proctitis.

The teachings provided herein are also directed to a method of treating a hemorrhoid while minimizing tissue damage and substantially reducing post-procedural pain. Generally speaking, the methods can include identifying a rectal tissue that comprises a vascular supply to a hemorrhoid, folding the rectal tissue to create a fold, securing the fold, and occluding the vascular supply to the hemorrhoid to facilitate an ischemic regression of the hemorrhoid, wherein the folding, securing, and occluding are all done gently to avoid a removal and/or a necrosis of the rectal tissue. As such, one of skill will appreciate having gentle methods of treatment that result in substantially less post-procedural pain over existing, state-of-the-art treatments. One of skill will appreciate that early hemorrhoids are often currently treated using rubber banding devices and infrared coagulation, for example, and advanced hemorrhoids are often currently treated using staples or Doppler-guided suture-based techniques, such as the popular PPH procedure (Procedure for Prolapse and Hemorrhoids) that respectively excises or suture-ligates the superior hemorrhoidal blood supply and pulls the prolapsed hemorrhoidal tissue into the anal canal.

The term "substantially" can be used, for example, to refer to an amount that one of skill would consider to be marked improvement over the comparison. In some embodiment, a substantial improvement can be a greater that 20%. In some embodiments, a substantial improvement can be greater than 30%, 40%, or 50%. In some embodiments, a substantial improvement can be greater than 60%, 70%, or 80%. And, in some embodiments, a substantial improvement can be greater than 90%, 95%, or 99%. Also, the perception of pain varies significantly from patient to patient, depending on culture, gender, age, social status, previous experience with pain, and other factors. Without intending to be limited to any theory or mechanism of action, what is mild discomfort or "no pain" for one person, could be expressed as painful or somewhat painful by another, etcetera. As a result, it should also be appreciated that one of skill could consider a post-procedural sensation to be "relatively painless," for example, when the majority of the patients, such as greater than 50%, 60%, 70%, or 80% of the patients in some embodiments, define or describe the sensation as painless including, for example, a sensation without pain or a sensation having mild-to-moderate discomfort only.

The PPH method is an example of a procedure that, although popular, creates a substantial trauma to the subject, and often much more trauma than is needed to treat a target area having a small lesion. The procedure includes pulling prolapsed tissue into a device for excision, the device having circular stapling mechanism for stapling the remaining unexcised tissue circumferentially around the target region of the rectoanal region having the hemorrhoid. And, this circumferential trauma is required by this technique, even if the pathology is focal. As a result, there are substantial risks with this method that include, for example, (i) the substantial trauma that creates a substantial amount of post-procedural pain; (ii) pulling too much muscle tissue into the device and excising the muscle with the hemorrhoid; (iii) sepsis from the trauma; and (iv) the possibility of chronic pain and chronic fecal urgency after the procedure. The PPH procedure is an example of a procedure that is not only significantly traumatic to the patient and, as a result, is typically performed by a colorectal surgeon, but it's also capital intensive. Once popular, this method has a growing disfavor in the surgical community. Suture-based devices are in development, as they can be effective with less pain, but these still suffer the need for high capital equipment, a steep learning curve, and for at least these reasons, a growing disfavor among surgeons.

Figure 2:
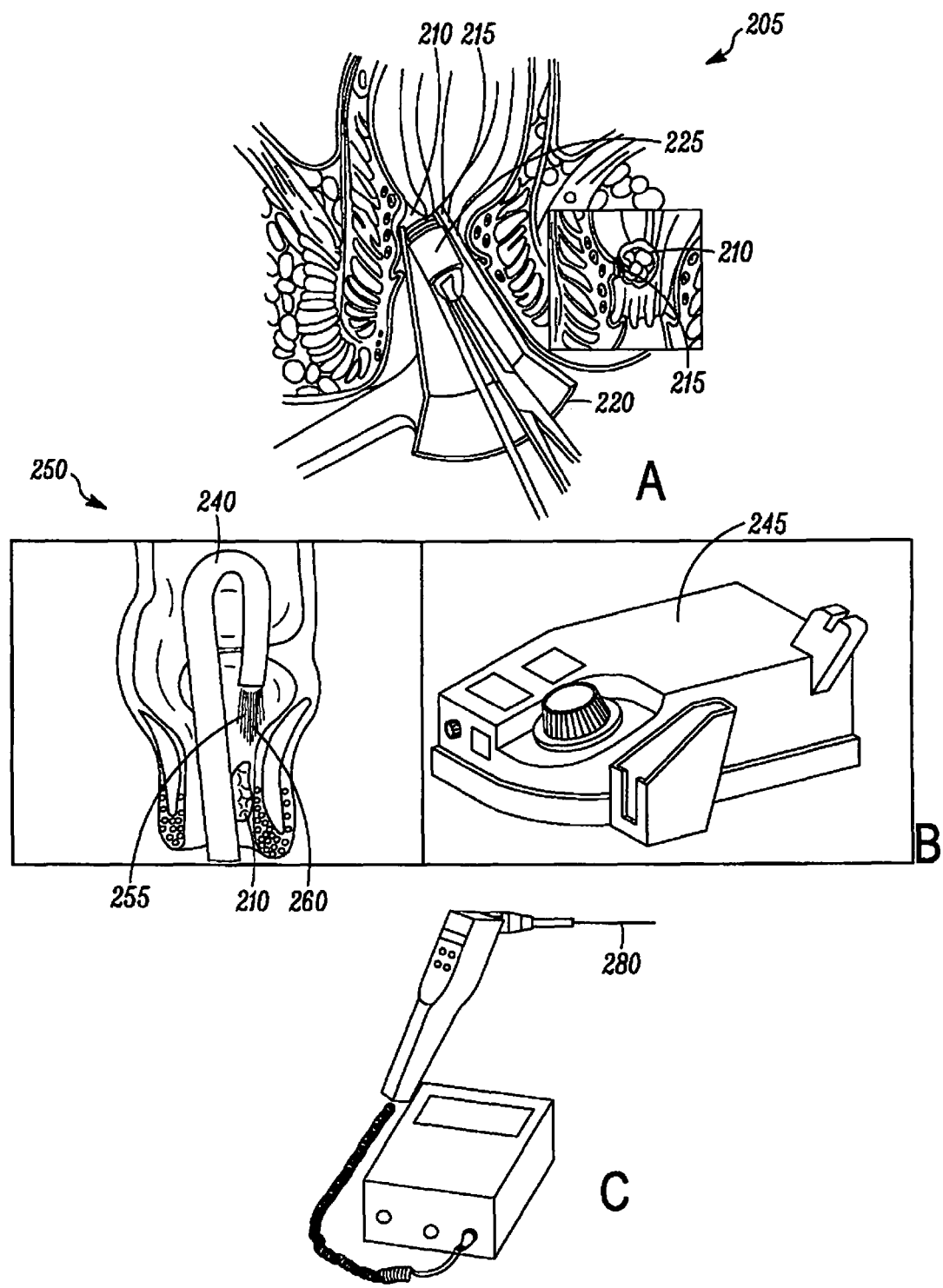
FIGS. 2A-2C illustrate state-of-the-art treatment methods that produce significantly more post-procedural pain than the gentle treatments set-forth herein.

FIGS. 2A-2C illustrate state-of-the-art treatment methods that produce significantly more post-procedural pain than the gentle treatments set-forth herein. FIG. 2A illustrates a rubber band ligation 205, which includes a strangulation of a small portion of the hemorrhoid 210 with a rubber band 215. The method uses an anoscope 220 with a rubber band delivery device 225. As with the PPH procedure, there is substantial post-procedural pain for about 5-7 days, substantial discomfort in the subject, a limited success rate, and is a procedure that is considered tedious with a steep learning curve and, as a result, is typically performed by a colorectal surgeon. FIG. 2B illustrates an infrared coagulation method that uses an endoscope 240 and an energy delivery device 245, the system 250 of which can be considered capital intensive and cumbersome. In addition, such methods are considered ineffective, being labeled as a method of "shooting-in-the-dark" with a small focus of energy 255 at a small and hard-to-locate target 260 for treatment of the hemorrhoid 210. FIG. 2C illustrates a heat and energy based method that is designed for a direct destruction of the hemorrhoid 210 with a monopolar electrical probe 280. As with other the state-of-the-art methods, the destruction creates an excessive tissue trauma, and significant pain to the subject. Moreover, the procedure requires a prolonged, tedious application time of about 15 minutes to about 30 minutes, as well as high capital equipment costs.

Figure 3:
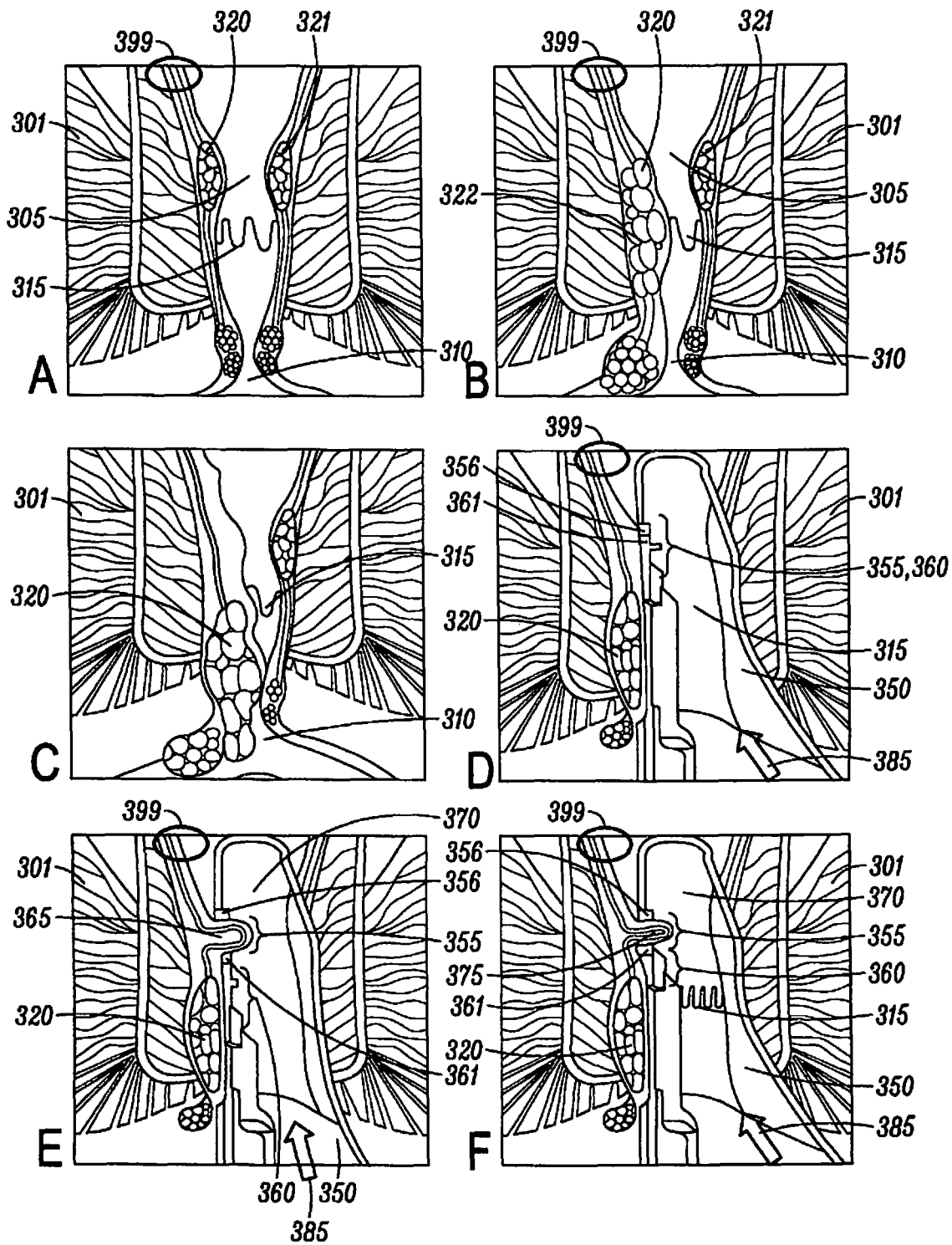
FIGS. 3A-3F illustrate a method of treating a prolapsed hemorrhoid, according to some embodiments.

FIGS. 3A-3F illustrate a method of treating a prolapsed hemorrhoid, according to some embodiments. As shown in FIG. 3A, internal hemorrhoids 320,321 are forming in a subject 301 in the subject's rectum 305 orally to the dentate line 315. FIG. 3B shows the manner in which an internal hemorrhoid 320 can become mobile and move toward the anus 310 due to the bulk and weight of the increased volume of blood 322 in the vasculature of the hemorrhoid 320. FIG. 3C shows the internal hemorrhoid 320 after it has prolapsed exterior to the anus 310. FIG. 3D shows the insertion of a therapeutic anoscope 350 as taught herein. The anoscope 350 includes a window 355 having a shutter 360 that is positioned orally to the dentate line 315 and opened for an entry of rectal tissue 365 into the lumen 370 of the anoscope 350.

The method can include inserting the anoscope 350 into the anus 310 of the subject 301 having the hemorrhoid 320, the anoscope 350 operable for (i) forming a fold 375 in the rectal tissue 365 orally to the hemorrhoid 320 and above the dentate line 315 in the subject 301; (ii) gently securing the fold 375; (iii) creating a work space 380 above the dentate line 315; and, (iv) providing a visualization 385 of the rectal tissue 365 without use of other apparatus such as, for example, an image transmission through optical fibers. As shown in FIG. 3F, the method can include gently securing the fold 375 in the rectal tissue 365 using a limited pressure between pinching surfaces 356,361 created by the shutter 360 and the window 355 to avoid a removal or a necrosis of the rectal tissue 365, the fold 375 having the vascular supply 399 for the hemorrhoid 320. Finally, the method can include occluding the vascular supply 399 to the hemorrhoid in a targeted manner to otherwise avoid damage to the rectal tissue 365, the occluding including a component selected from the group consisting of heat, energy, ligation, or a combination thereof. In addition to the other benefits set-forth herein, the gentle methods provided can result in substantially less post-operative pain than a method of treating hemorrhoids that does not avoid the removal or the necrosis of the rectal tissue. As shown in FIGS. 3A-3F, the methods can be used to treat most any condition that could benefit from an ischemic regression of a hemorrhoid, including the preventing, inhibiting, reducing, or eliminating of a prolapse of the hemorrhoid.

The methods can include gently securing a fold of rectal tissue comprising the vascular supply to the hemorrhoid, and the gently securing can include any method known to one of skill that is gentle enough to avoid a significant trauma to the patient while effective enough to obtain the occlusion of the vascular supply to the hemorrhoid that leads to the ischemic regression of the hemorrhoidal tissue. The term "effective," can be used to describe an amount or a result that obtains, either in full or at least substantially, a desired outcome. For example, if an ischemic regression of a tissue is sought through an occlusion of a vascular supply to the tissue, the occlusion can be considered effective where there is at least some ischemic regression, at least in some embodiments. In some embodiments, the outcome can be at least substantially obtained where there is a desired reduction in the degree or extent of symptoms present. For example, a desired reduction can be substantial, in some embodiments, where the degree or extent of symptoms is reduced by 20%, 30%, 40%, 50%, 60%, 70%, 80%, 90%, 100%, or any 5% increment therein. In some embodiments, an outcome can be at least substantially obtained where the outcome is obtained in a reasonable amount of time. A reasonable amount of time may be, for example, 1 week, 2 weeks, 1 month, 2 months, 3 months, 6 months, or the like, depending on the type and extent of outcome desired.

Figure 4:
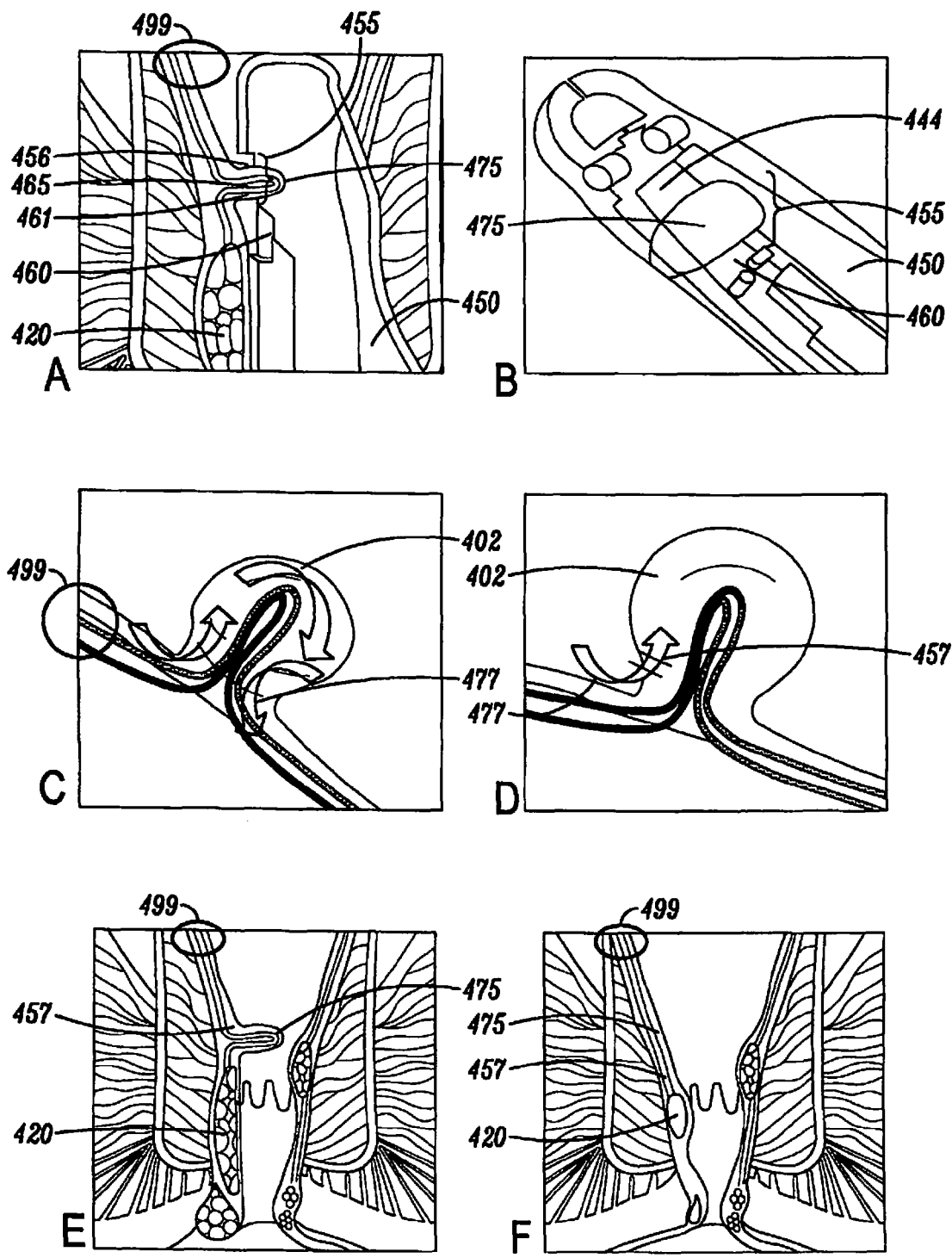
FIGS. 4A-4F illustrate the occlusion of the vascular supply to the hemorrhoid that leads to the ischemic regression of the hemorrhoidal tissue, according to some embodiments.

FIGS. 4A-4F illustrate the occlusion of the vascular supply to the hemorrhoid that leads to the ischemic regression of the hemorrhoidal tissue, according to some embodiments. As shown in FIG. 4A, the gently securing can be used to create a constant tissue fold configuration 402 to facilitate the occluding of the vascular supply 499 to the hemorrhoid 420. FIG. 4A also shows a means for securing the fold 475 with a controlled pressure using the therapeutic anoscope 450 to provide the constant tissue fold configuration 402 to the rectal tissue 465. The structure of the means can include opposing pinching surfaces 456, 461 having, for example a distal contact surface 456 of the window 455 that is opposing a distal contact surface 461 of the shutter 460. The controlled pressure 403 can be provided by any means for controlling the pressure, or force per unit area, applied to the rectal tissue 465. The terms "controlled" and "limited" can be used interchangeably, in some embodiments. In some embodiments, a pressure is "controlled" where the user has substantial control over the amount of pressure applied, and the type of control can include a variety of control mechanisms known to one of skill. In some embodiments, a pressure is "limited" where there is a pressure-governing mechanism in place, and the type of governing can include a variety of governing mechanisms known to one of skill. It should be appreciated that pressure can be regulated as any form of pressure, for example, mechanical, pneumatic, hydraulic, or the like, where one of skill can control or limit pressure using known methods.

The methods can include the use of a limited pressure on the rectal tissue for the gently securing of the fold, such that the tissue damage is avoided, prevented, or substantially prevented. Any mechanism known to one of skill in the art can be used to control or limit the amount of pressure applied to the tissue to avoid damage to the tissue. In some embodiments, a means for controlling the pressure, or force per unit area, can include, for example, a spring mechanism that limits the pressure applied to the rectal tissue 465 to what is applied by the spring to the pinching surfaces 456, 461, the spring preventing a user from applying a pressure greater than the pressure that creates a compression of the spring. In some embodiments, a means for controlling the pressure, or force per unit area, can include, for example, a material having a modulus of elasticity that prevents a user from applying a pressure greater than the pressure that creates a strain of the material. In some embodiments, a means for controlling the pressure, or force per unit area, can include, for example, a material having a hardness that prevents a user from applying a pressure greater than the pressure that creates a compression of the material. In some embodiments, a component in the anoscope or treatment system including the anoscope, can include any one or any combination of such pressure limiting systems.

The methods can include occluding the vascular supply to the hemorrhoid in a targeted manner to avoid unnecessary tissue damage. The occluding can be achieved using any method known to one of skill, to the extent that the method is gentle enough to avoid trauma to the patient while effective enough to obtain the ischemic regression of the hemorrhoidal tissue. The occluding, for example, can include a selective and focused application of heat, energy, ligation, or a combination thereof, to the vascular supply to the hemorrhoid, the application limited to occluding the vascular supply while otherwise avoiding damage to the tissue. As such, the method can be applied in a targeted manner to avoid trauma to the patient.

FIG. 4B shows the application of heat 444 to the rectal tissue 465 in combination with the gently securing of the rectal tissue 465. FIG. 4C shows the vascular supply 499 after the gently securing, still flowing venous and arterial blood through the fold 402 and to the hemorrhoid 420, after which the heat 444 is applied for the occlusion 455 of the blood flow 477. FIG. 4E shows an ischemic regression 466 of the hemorrhoid 420 after the occlusion 455 has been obtained. The fold 475 remains in place and regresses over time as well, as shown in FIG. 4F. FIG. 4F illustrates a successful treatment.

The pressure used to gently secure the fold can vary according to a number of factors. One of skill will appreciate, for example, that not all tissue will respond to pressure in the same manner, as there are variations within and between subjects due to any number of reasons known in the art, including heterogeneity of tissue within and between patients, the age of the patient, the patient's health and/or condition treated, and the like. And, it will be appreciated that the response of tissue to increases in pressure may not be linear, in some embodiments, as increased forces applied to small contact areas may cause proportionally more damage to tissue when compared to equal pressures applied to the same tissue using relatively larger contact areas. Likewise, temperature can have an effect, as the application of pressure to a tissue can show an increased amount of damage to the tissue when the pressure is applied at an increased temperature.

In some embodiments, the limited pressure can range from, for example, about 50 kPa to about 1000 kPa, about 50 kPa to about 750 kPa, about 50 kPa to about 500 kPa, about 75 kPa to about 800 kPa, about 100 kPa to about 600 kPa, about 100 kPa to about 300 kPa, about 50 kPa to about 400 kPa, about 50 kPa to about 250 kPa, about 25 kPa to about 500 kPa, about 500 kPa to about 1000 kPa, about 500 kPa to about 750 kPa, about 750 kPa to about 1000 kPa, or any range therein. In some embodiments, the limited pressure can be about 10 kPa, about 20 kPa, about 30 kPa, about 40 kPa, about 50 kPa, about 60 kPa, about 70 kPa, about 80 kPa, about 90 kPa, about 100 kPa, about 110 kPa, about 120 kPa, about 130 kPa, about 140 kPa, about 150 kPa, about 160 kPa, about 170 kPa, about 180 kPa, about 190 kPa, about 200 kPa, 210 kPa, about 220 kPa, about 230 kPa, about 240 kPa, about 250 kPa, about 260 kPa, about 270 kPa, about 280 kPa, about 290 kPa, about 300 kPa, 310 kPa, about 320 kPa, about 330 kPa, about 340 kPa, about 350 kPa, about 360 kPa, about 370 kPa, about 380 kPa, about 390 kPa, about 400 kPa, about 500 kPa, about 600 kPa, about 700 kPa, about 800 kPa, about 900 kPa, about 1000 kPa, or any 5 kPa increment therein.

In some embodiments, a contact area of a pinching surface can range from about 20 $mm^2$ to about 1000 $mm^2$, from about 20 $mm^2$ to about 1000 $mm^2$, from about 40 $mm^2$ to about 800 $mm^2$, from about 50 $mm^2$ to about 500 $mm^2$, from about 75 $mm^2$ to about 750 $mm^2$, from about 90 $mm^2$ to about 900 $mm^2$, from about 100 $mm^2$ to about 300 $mm^2$, from about 175 $mm^2$ to about 400 $mm^2$, from about 200 $mm^2$ to about 500 $mm^2$, from about 40 $mm^2$ to about 400 $mm^2$ from about 45 $mm^2$ to about 450 $mm^2$, from about 50 $mm^2$ to about 100 $mm^2$, or any range therein. In some examples the contact area of a pinching surface can be, for example, about 50 $mm^2$, about 60 $mm^2$, about 70 $mm^2$, about 80 $mm^2$, about 90 $mm^2$, about 100 $mm^2$, about 110 $mm^2$, about 120 $mm^2$, about 130 $mm^2$, about 140 $mm^2$, about 150 $mm^2$, about 160 $mm^2$, about 170 $mm^2$, about 180 $mm^2$, about 190 $mm^2$, about 200 $mm^2$, about 210 $mm^2$, about 220 $mm^2$, about 230 $mm^2$, about 240 $mm^2$, about 250 $mm^2$, about 260 $mm^2$, about 270 $mm^2$, about 280 $mm^2$, about 290 $mm^2$, about 300 $mm^2$, or any 5 $mm^2$ increment therein.

In some embodiments, the force applied to a contact area can range from about 100 g to about 5000 g, from about 200 g to about 4000 g, from about 300 g to about 3000 g, from about 200 g to about 2000 g, from about 300 g to about 1000 g, from about 500 g to about 1000 g, or any range therein. In some embodiments, the force can be about 200 g, 300 g, 400 g, 500 g, 600 g, 700 g, 800 g, 900 g, 1000 g, 1100 g, 1200 g, 1300 g, 1400 g, 1500 g, 1600 g, 1700 g, 1800 g, 1900 g, 2000 g, 2100 g, 2200 g, 2300 g, 2400 g, 2500 g, 2600 g, 2700 g, 2800 g, 2900 g, 3000 g, 3100 g, 3200 g, 3300 g, 3400 g, 3500 g, 3600 g, 3700 g, 3800 g, 3900 g, 4000 g, or any 10 g increment therein.

In some embodiments, the targeted manner can include heating at a temperature of about 50° C. to about 65° C. for an effective time to selectively coagulate the vascular supply during the occluding while avoiding the removal or the necrosis of the rectal tissue. In some embodiments, the targeted manner includes heating at a temperature of about 50° C. to about 65° C. for an effective time, the heating including applying an energy from a plurality of discrete regions on the pinching surfaces to a corresponding plurality of discrete areas on the fold to selectively coagulate the vascular supply during the occluding while preserving the remainder of the fold to avoid the removal or the necrosis of the rectal tissue fold. In some embodiments, the heating can be at a temperature ranging from about 30° C. to about 70° C., from about 35° C. to about 65° C., from about 40° C. to about 60° C., from about 45° C. to about 55° C., from about 50° C. to about 65° C., or any range therein. In some embodiments, heating can be at a temperature of about 40° C., about 45° C., about 50° C., about 55° C., about 60° C., about 65° C., about 70° C., or any 1° C. increment therein.

The heating can be applied for a limited amount of time, or obtained or applied by ramping to the temperature over a period of time. Accordingly, the temperature can be applied as a constant temperature for an effective time, a ramping to a temperature over an effective time, a ramping to a temperature that is applied for an effective time, a ramping down from a temperature, or any combination thereof. One of skill will appreciate that the selection of the desired temperature/time procedure for applying an occlusion energy, for example, will be a function of occluding the vascular supply to the hemorrhoid most effectively with the least tissue damage. In some embodiments, the heating can be applied for a time ranging from about 1 sec to about 120 seconds, from about 5 sec to about 90 seconds, from about 10 sec to about 60 seconds, from about 5 sec to about 30 seconds, from about 1 sec to about 5 seconds, from about 5 sec to about 10 seconds, from about 10 sec to about 30 seconds, or any range therein. In some embodiments the ramping time to a temperature can range from about 1 sec to about 120 seconds, from about 5 sec to about 90 seconds, from about 10 sec to about 60 seconds, from about 5 sec to about 30 seconds, from about 1 sec to about 5 seconds, from about 5 sec to about 10 seconds, from about 10 sec to about 30 seconds, or any range therein. An "effective amount of time" or an "effective time" is the amount of time that produces a desired extent of occlusion of the vascular supply to the hemorrhoid. In some embodiments, the vascular supply can be occluded during an effective amount of time by 75%, 80%, 85%, 90%, 95%, 97%, 99%, 100%, or any 1% increment therein. In some embodiments, the effective amount of time can result in less than 100% occlusion, and the vascular supply reaches 100% occlusion without further therapy. In some embodiments, less than 100% occlusion is desired during the effective time to avoid unnecessary damage to tissue and still achieve ischemic regression of the hemorrhoid.

The application of heat and/or energy in the occlusion can be absent in some embodiments. In some embodiments, for example, the targeted manner includes gently securing the fold into a constant tissue fold configuration for a suturing of the rectal tissue orally to the hemorrhoid to selectively ligate the vascular supply to the hemorrhoid. A careful suturing that otherwise avoids the removal or the necrosis of the rectal tissue again avoids damage to the tissue, substantially reducing trauma and an associate post-procedural pain to the patient. In some embodiments, however, the suturing can be accompanied by an application of heat and/or energy as taught herein.

Figure 5:
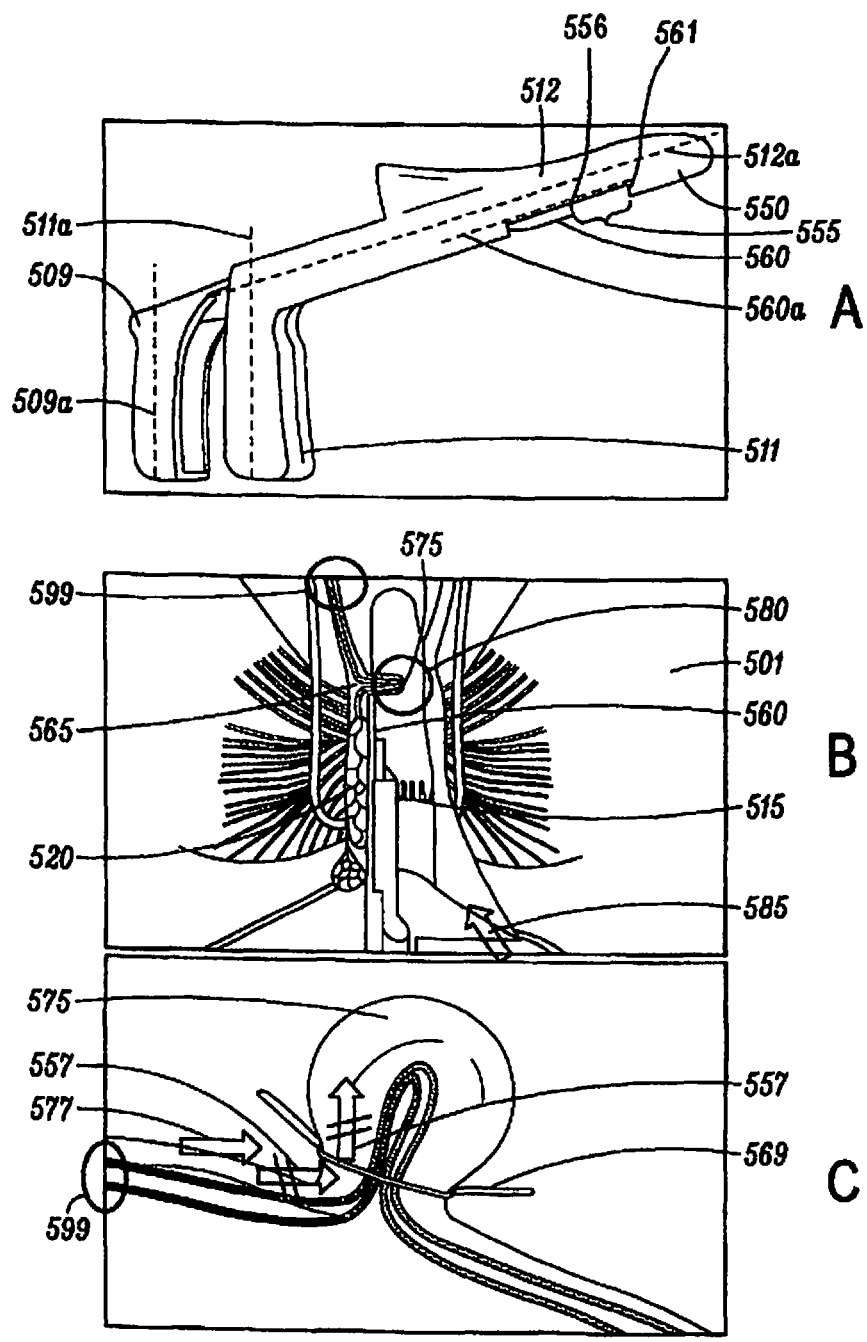
FIGS. 5A-5C illustrate a method and device for gently securing and suturing a fold of rectal tissue above a dentate line and orally to a hemorrhoid, according to some embodiments.

FIGS. 5A-5C illustrate a method and device for gently securing and suturing a fold of rectal tissue above a dentate line and orally to a hemorrhoid, according to some embodiments. FIGS. 5A and 5B illustrate a therapeutic anoscope 550 operable for (i) forming a fold 575 in the rectal tissue 565 orally to the hemorrhoid 520 and above the dentate line 515 in the subject 501; (ii) gently securing the fold 575; (iii) creating a work space 580 above the dentate line 515; and, (iv) providing a visualization 585 of the rectal tissue 565 without use of other apparatus such as, for example, an image transmission through optical fibers. As shown in FIG. 5B, the method can include gently securing the fold 575 in the rectal tissue 565 using a limited pressure between pinching surfaces 556, 561 created by the shutter 560 and the window 555 to avoid a removal or a necrosis of the rectal tissue 565, the fold 575 having the vascular supply 599 for the hemorrhoid 520. Finally, FIG. 5C shows that the method can include occluding the vascular supply 599 to the hemorrhoid in a targeted manner to otherwise avoid damage to the rectal tissue 565, the occluding 555 including a suturing 569 to ligate the vascular supply 599 and stop or reduce the flow of blood 577 to ischemically regress the hemorrhoid 520. The anoscope is shown in FIG. 5A as having a proximal handle 509 and a distal handle 511 operably attached to the shutter 560, the proximal handle 509 slidably attached to the distal handle 511, such that the longitudinal axis 560a of the shutter 560 slides in a direction that is parallel or substantially parallel to the longitudinal axis 512a of the body 512 of the anoscope 550. The longitudinal axis 509a of the proximal handle 509 and/or the longitudinal axis 511a of the distal handle 511 can be in a pistol-grip orientation to the longitudinal axis 512a of the body 512 to allow for a comfortable grip and manipulation of the anoscope 550 during use.

The controlled or limited pressure, or force per unit area, can come from any configuration or orientation that gently secures the fold. In some embodiments, the body of the anoscope has a central axis, and the controlled pressure is applied at an angle ranging from about 0 degrees to about 90 degrees from the central axis. In some embodiments, the orientation in which the controlled pressure is applied can be adjusted in the anoscope. In some embodiments, the adjusting of the orientation can be done outside of the patient's body and, in some embodiments, after insertion of the anoscope into the patient's body, for example, in situ during a procedure to avoid a need to remove, adjust, and re-insert the therapeutic anoscope.

The teachings are also directed to a anoscope used with the methods taught herein. An anoscope used in the methods can comprise any scaffolding structure and means for performing the steps of the methods described herein, namely identifying a rectal tissue that comprises a vascular supply to a hemorrhoid, folding the rectal tissue to create a fold, securing the fold, and occluding the vascular supply to the hemorrhoid to facilitate an ischemic regression of the hemorrhoid, wherein the folding, securing, and occluding are all done gently to avoid a removal and/or a necrosis of the rectal tissue. For example, any means for creating the work space in the subject can be fashioned for use as an anoscope, and any means for gently securing a fold of tissued orally to the hemorrhoid and above the dentate line can also be used in the occluding. The means for creating the work space can be, for example, a static or dynamically expandable framework of panels or struts, an inflatable scaffolding, a rigid cylinder, a transparent structure, and the like, the scaffolding having a means for receiving a rectal tissue to facilitate gently securing a fold in the rectal tissue for gently occluding the vascular supply to the hemorrhoid. In some embodiments, the work space can be creating using a cylindrical, or substantially cylindrical, body for insertion into the subject, the cylindrical body creating a work space having a sufficient volume to perform the occluding of the vascular supply to the hemorrhoid. In such embodiments, the cylindrical, or substantially cylindrical, body can comprise a side window and, optionally, a convex surface or bulge that can be designed to help promote an entry of the rectal tissue into the window for the gently securing of the rectal tissue. In some embodiments, the body of the anoscope is operably attached to a distal handle, and the distal handle is operable attached to a proximal handle, the proximal handle being operably attached to a shutter component for closing the window and applying a controlled, or limited, pressure to a rectal tissue. Consistent with the teachings herein, the controlled, or limited, pressure is a design feature that's incorporated by mechanism, materials, or a combination thereof, into the anoscope to avoid applying an amount of pressure that unnecessarily creates tissue damage. In some embodiments, the anoscope can have a pistol-grip configuration, as shown in FIG. 5A, for example, making the device easy for a user to hold and manipulate during a treatment. A pistol-grip configuration can be configured, for example, such that the longitudinal axis of the proximal and/or distal handle can have an angle with the axis of the body that is about 20°, about 25°, about 30°, about 35°, about 40°, about 45°, or any 1° increment therein.

FIGS. 6A-6D illustrates a therapeutic anoscope for treating a hemorrhoid in a subject while avoiding a trauma associated with removing a rectal tissue, according to some embodiments. The therapeutic anoscope 650 can include a cylindrical, or substantially cylindrical, anoscope body 612 having a lumen 614, a proximal opening 616, a distal end 618 configured for a first point of entry into an anus of a subject, and a side window 655 having a shutter 660 and pinching surfaces 656,661 to form a fold in a rectal tissue orally to a hemorrhoid. The pinching surfaces 656,661 can be configured to gently secure the fold 575 with a limited pressure above a dentate line in a subject. The anoscope body 612 can have any configuration that will support a visualization, and a gentle tissue capturing and securing mechanism that will operably function as taught using the methods taught herein.

Figure 6:
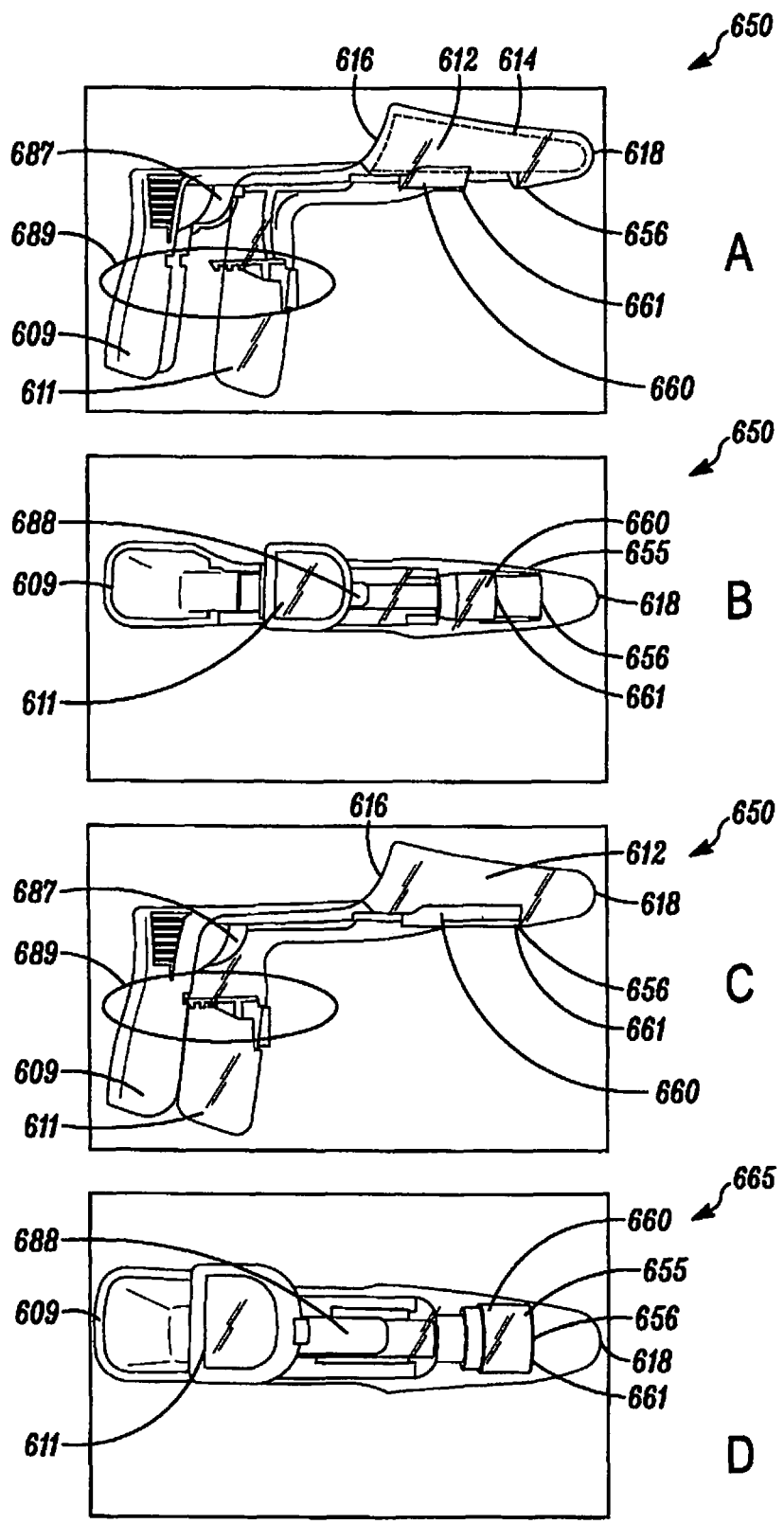
FIGS. 6A-6D illustrates a therapeutic anoscope for treating a hemorrhoid in a subject while avoiding a trauma associated with removing a rectal tissue, according to some embodiments.

FIGS. 6A-6D show a proximal handle 609 and a distal handle 611 in a pistol-grip orientation with the body 612 of the anoscope 650. The proximal handle 609 is operable attached to the shutter 660 and the distal handle 611. The distal handle 611 is operably attached to the body 612. FIGS. 6A and 6B show a side and bottom view of the anoscope 650 in a shutter-open position, and FIGS. 6C and 6D show a side and bottom view of the anoscope 650 in a shutter-closed position. FIGS. 6B and 6D show a portion of a retraction coil spring 688 that provides a tension for retracting the shutter from the shutter-closed position to the shutter-open position. And, FIGS. 6A and 6C show a latch-type locking mechanism 689 for securing the shutter 660 in the shutter-closed position. The shutter-closed position includes the slightly retracted position of the shutter 660 as described herein in which a tissue is gently secured under a controlled, or limited, pressure for the occlusion of the vascular supply to the hemorrhoid. This is because the shutter 660 can be operably and slidably attached to the proximal handle, for example, using a compression coil spring 687 (not shown) that limits the amount of pressure that can be applied by the pinching surfaces 656,661 to the fold of tissue.

Figure 7:
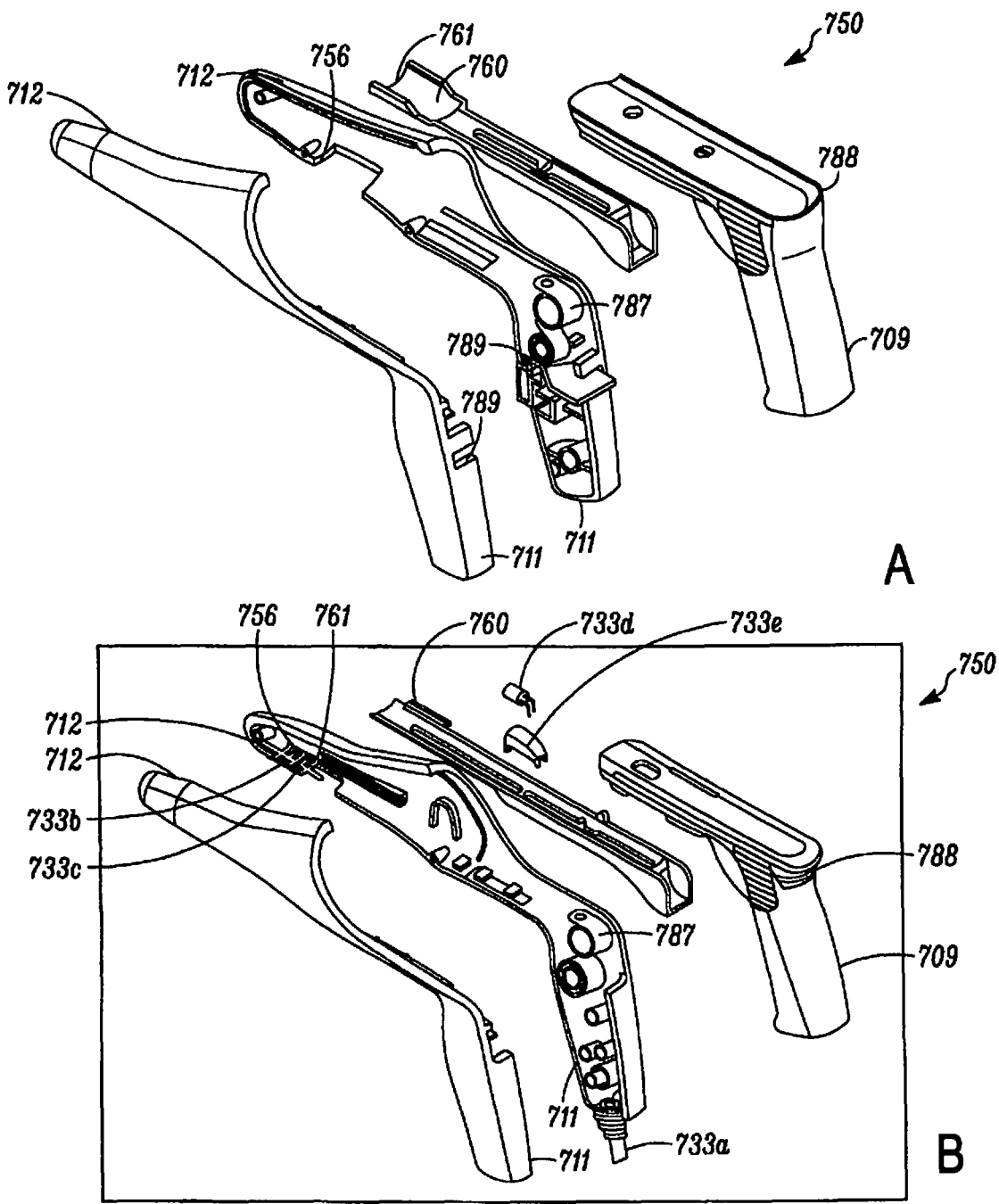
FIGS. 7A and 7B illustrate an exploded view of therapeutic anoscopes with and without components for delivering energy for occlusion of a vascular supply to a hemorrhoid, according to some embodiments.

FIGS. 7A and 7B illustrate an exploded view of therapeutic anoscopes with and without components for delivering energy for occlusion of a vascular supply to a hemorrhoid, according to some embodiments. The anoscope 750 has a proximal handle 709 and a distal handle 711. The proximal handle 709 is operable attached to the shutter 760. The distal handle 711 and the body 712 are formed in a two-piece assembly configuration, whereas the shutter 760 and the proximal handle 709 are each single-piece units. The distal handle is operably attached to the body in a pistol-grip configuration. FIGS. 7A and 7B show a compression coil spring 787 that limits the amount of pressure that can be applied by the pinching surfaces 756,761 to the fold of tissue. There is also a retraction coil spring 788 (not shown) that provides a tension for retracting the shutter from the shutter-closed position to the shutter-open position. A latch-type locking mechanism 789 is also provided for securing the shutter 760 in the shutter-closed position. The shutter-closed position includes the slightly retracted position of the shutter 760 as described herein in which a tissue is gently secured under a controlled, or limited, pressure for the occlusion of the vascular supply to the hemorrhoid. This is because the shutter 760 can be operably and slidably attached to the proximal handle, for example, using the compression coil spring 787 that limits the amount of pressure that can be applied by the pinching surfaces 756,761 to the fold of tissue. FIG. 7B also shows electrical components 733a,733b,733c,733d,733e for delivering an energy to the pinching surfaces 756,761 for occluding the vascular supply the hemorrhoid. Input 733a provides a circuit for the flow of an energy through a window contact 733b and a shutter contact 733c as they are brought a sufficiently close proximity for the transfer of the energy, such as during the gently securing of the fold of rectal tissue to occlude the vascular supply to the hemorrhoid. Connectors 733d,733e provide a connection between the input 733a and the shutter contact 733c. As the contacts 733b,733c are brought in close proximity during the gently securing of the tissue, the circuit closes, energy passes, and the occlusion of the vascular supply occurs.

The pinching surfaces can have any configuration that one of skill believes will effectively pinch and gently secure a fold of rectal tissue as described herein. In some embodiments, the pinching surfaces can be arcuate in shape to facilitate the grasping or pinching of the tissue as it enters the window of the body of the anoscope. The arcuate shape can reflect the convex shape of the body in regions adjacent to the window. Likewise, the shutter can also have an arcuate shape. The pinching surfaces can also have a contact surface that is smooth or rough, with raised protrusions, dimples, ridges, and the like. In some embodiments, the pinching surfaces can have a series of vertical small electrodes having gaps in-between the electrodes. An example of such a configuration could include serrations, channels, or grooves, of any of a variety of configurations. Such an arrangement can provide an application of energy in spots or islands, rather than uniformly across the pinching surface, to allow delivery of more energy to a thicker tissue in a focused manner, allowing tissue to remain untreated between the gaps to help ensure a minimal amount of damage to the rectal tissue and, at least, avoid necrosis in the tissue fold.

Energy can be applied to the fold selectively, and in a targeted manner, in some embodiments. That is, in some embodiments, energy is not applied all around the tissue tissue fold but, rather, is selectively applied in a targeted manner to occlude the vascular supply to the hemorrhoid while pursuing the least damage to the surrounding, collateral tissue. In some embodiments, the result of the application of energy includes coagulated vessels, sclerosis, and no substantial necrosis in the tissue fold. In some embodiments, the tissue fold can be between about 1 mm to about 6 mm in thickness when compressed. And, in some embodiments, the tissue fold can be between about 2 mm to about 4 mm in thickness when compressed. In some embodiments, the thickness of the tissue fold can be about 0.5 mm, 1.0 mm, 2.5 mm, 3.5 mm, 4.5 mm, 5.5 mm, 6.5 mm, 7.5 mm, or any 0.5 mm increment therein. As described herein, the effective treatment time for an application of energy can vary. It should be appreciated that heterogeneity of tissue can naturally be a part of a tissue fold, and the thickness and heterogeneity of tissue can affect the treatment time that is found to be effective. In some embodiments, the temperature of an applied heat ranges from about 50° C. to about 65° C., and the treatment time can range, for example, from about 8 seconds to about 25 seconds.

In some embodiments, a heterogeneous tissue fold can be exposed to a moderate temperature, between about 50° C. and about 65° C., and the tissue is simultaneously compressed. The pressure, temperature, and time of application of energy is balanced to target the endothelium of the vessels and some submuscosa, and the collateral tissue is spared. The entire fold becomes moderately ischemic and form a beneficial scar.

Figure 8:
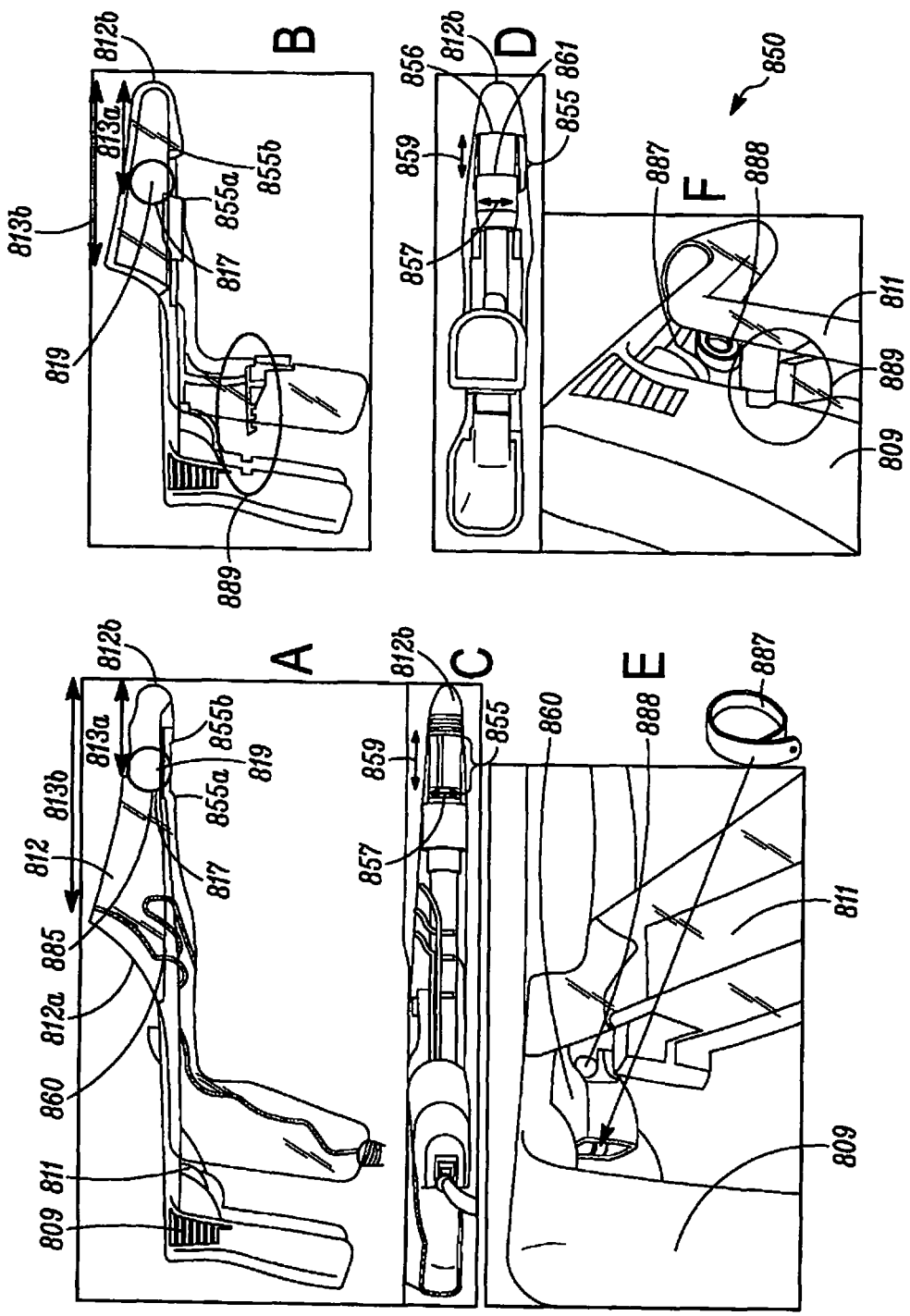
FIGS. 8A-8F illustrate aspects of therapeutic anoscopes with and without components for delivering energy for occlusion of a vascular supply to a hemorrhoid, according to some embodiments.

FIGS. 8A-8F illustrate aspects of therapeutic anoscopes with and without components for delivering energy for occlusion of a vascular supply to a hemorrhoid, according to some embodiments. FIGS. 8A and 8C show an anoscope 850 configured for delivering energy without any additional system components, save for an energy source (not shown), whereas FIGS. 8B and 8D show an anoscope 850 that is not configured to deliver an energy in the absence of a separate system component, meaning that the anoscope 850 in FIGS. 8B and 8D could be used with the delivery of an energy, but the energy would derive from a separate component through the body 812. As can be seen in FIGS. 8A and B, the body 812 can be transparent or translucent to assist the user of the anoscope 850. In some embodiments, the anoscope body 812 can be configured for providing a length 813 sufficient to position the pinching surfaces 856,861 above the dentate line in the subject. The length 813 can include two component distances, such as a window distance 813a and a viewing port distance 813b. Window distance 813a is the distance from the distal end 812b of the anoscope body 812 to the proximal side 855a of the window 855. The viewing port distance 813b is the distance from the distal end 812b of the anoscope body 812 to the proximal end 812a of the anoscope body 812.

In some embodiments, the anoscope body 812 can be configured for providing a volume 817 in the lumen 819 sufficient for receiving the fold of the rectal tissue for the occluding of the vascular supply to the hemorrhoid. Volume can be considered proportional to diameter, in embodiments that use a round, or substantially round, cylindrically shaped body 812. The distal end 812b of the body 812 can range in diameter, for example, from about 1.0 cm to about 3.0 cm, from about 1.5 cm to about 2.5 cm, from about 1.6 cm to about 2.3 cm, from about 1.2 cm to about 2.7 cm, or any range therein. The region of the body 812 that includes the window 855 can range in diameter, for example, from about 1.0 cm to about 4.0 cm, from about 1.5 cm to about 3.5 cm, from about 1.8 cm to about 3.3 cm, from about 1.4 cm to about 2.0 cm, or any range therein. And, as taught herein, the region around the window 855 can have a convex region, or bulging portion, that can help facilitate entry of a rectal tissue into the window 855. The proximal end 812a of the body 812 can range in diameter, as well, and one of skill will be able to select a diameter that provides a visualization 885 of the fold for a particular device, as well as an adequate entry of another component as needed during a hemorrhoid treatment procedure. The anoscope 850 can be configured to (i) provide a visualization 895 of the rectal tissue without an image transmission through optic fibers and (ii) facilitate an ischemic regression of the hemorrhoid through the occluding to treat the hemorrhoid in a manner that provides substantially less post procedural pain to the subject than a hemorrhoid treatment procedure that does not avoid the removal or the necrosis of the rectal tissue.

The window 855 of the anoscope 850 can have dimensions that facilitate entry of the rectal tissue into the window 855. In some embodiments, the window 855 can have a width 855a ranging from about 0.5 cm to about 2.5 cm, from about 0.75 cm to about 2.25 cm, from about 1.0 cm to about 2.0 cm, from about 0.75 cm to about 1.75 cm, or any range therein. In some embodiments, the window 855 can have a length from about 0.5 cm to about 3.5 cm, from about 0.75 cm to about 3.0 cm, from about 1.0 cm to about 2.5 cm, from about 0.75 cm to about 2.75 cm, or any range therein.

In some embodiments, the shutter 860 can be configured for opening the window 855 to allow the rectal tissue to enter the window 855 during the treatment of the hemorrhoid in the subject; creating the fold in the rectal tissue orally to the hemorrhoid; and, gently securing the fold with the limited pressure above the dentate line to avoid the removal or the necrosis of the rectal tissue that creates the trauma to the subject. And, as shown in FIGS. 8E and 8F, and as otherwise described herein, the anoscope 850 can have a retraction coil spring 888 and a compression coil spring 887, the retraction coil spring provide a tension for returning the shutter from a closed, or tissue securing, position to an open position, and the compression coil spring controlling, or limiting, the pressure that can be applied to the rectal tissue by the pinching surfaces of the anoscope.

In some embodiments, the volume 817 is sufficient for a suturing to selectively ligate the vascular supply during the occluding while otherwise avoiding the removal or the necrosis of the rectal tissue fold. And, in some embodiments, the volume 817 is sufficient for an application of heat at a temperature of about 50° C. to about 65° C. for an effective time to selectively coagulate the vascular supply during the occluding while avoiding a necrosis of the rectal tissue fold. Moreover, in some embodiments, the volume 817 is sufficient for an application of an RF energy to selectively coagulate the vascular supply during the occluding while avoiding a necrosis of the rectal tissue fold. In some embodiments, the RF energy or heat can be applied such that the temperature is ramped at a desired rate and heated for an effective amount of time to occlude the vascular supply to the hemorrhoid while otherwise avoiding damage to tissue surrounding the vascular supply. The anoscope 850 also provides a visualization 885, a proximal handle 809, a distal handle 811, a shutter 860, and a locking mechanism 889.

In some embodiments, the anoscope body has a central axis, and the limited pressure is applied in the same, or substantially same, plane as a plane formed by the rectal tissue before the pinching, and at an angle ranging from about 0 degrees to about 90 degrees from the central axis. And, in some embodiments, the anoscope body is translucent or transparent.

In some embodiments, a therapeutic anoscope is presented for treating a prolapsed hemorrhoid in a subject in a manner that creates substantially less post-procedural pain. The anoscope can have a cylindrical, or substantially cylindrical, anoscope body having a lumen, a proximal opening, a distal end configured for a first point of entry into an anus of a subject. The body can also include a side window having a shutter and pinching surfaces to form a fold in a rectal tissue orally to a prolapsed hemorrhoid and gently secure the fold with a limited pressure above a dentate line in a subject. The anoscope body can be configured for providing a length sufficient to position the pinching surfaces above the dentate line in the subject; and, providing a volume in the lumen sufficient for receiving the fold of the rectal tissue for an occluding of a vascular supply to the hemorrhoid. The shutter can be configured for opening the window to allow the rectal tissue to enter the window during a treatment of a hemorrhoid in the subject; creating the fold in the rectal tissue orally to the prolapsed hemorrhoid; and, gently securing the fold with a limited pressure ranging from about 50 kPa to about 1000 kPa above the dentate line to avoid a removal or a necrosis of the rectal tissue that creates a trauma to the subject. It should be appreciated that, in some embodiments, the rectal tissue can incorporate at least a portion of a hemorrhoid in a rectal tissue fold where, in some embodiments, the entire hemorrhoid may be incorporated. And, the anoscope can function to (i) directly visualize the rectal tissue without an endoscope having optic fibers and (ii) facilitate an ischemic regression of the prolapsed hemorrhoid through the occluding. The anoscopes taught herein can be used to treat the hemorrhoid in a manner that provides substantially less post procedural pain to the subject than a procedure that does not avoid the removal or the necrosis of the rectal tissue that creates trauma to the subject, facilitating the ischemic regression that results in a loss of bulk and weight in the prolapsed hemorrhoid.

It should be appreciated that the pinching surfaces that gently secure the tissue can have any configuration known to one of skill to accomplish the act of gently securing the fold for the occluding of the vascular supply to the hemorrhoid. The configuration should provide a securing surface and pressure that is gentle enough to avoid trauma to the patient in a manner consistent with the teachings herein. In some embodiments, the pinching surfaces can have an arcuate shape to facilitate a recruiting of the rectal tissue into the lumen of the body of the anoscope. And, in some embodiments, the pinching surfaces have a plurality of discrete regions on the pinching surfaces corresponding to a plurality of discrete areas on the fold to selectively coagulate the vascular supply during the occluding while preserving the remainder of the fold to avoid the removal or the necrosis of the rectal tissue fold.

A system for treating a hemorrhoid in a subject in a manner that creates substantially less post-procedural pain is also provided herein. In some embodiments, the system comprises a therapeutic anoscope; and, an occlusion device operable for a targeted application of heat, energy, or ligation to the vascular supply to the hemorrhoid, the targeted application otherwise avoiding damage to the rectal tissue. In some embodiments, the occlusion device applies RF energy to the vascular supply to the hemorrhoid. In some embodiments, the occlusion device facilitates an application of a suture to the vascular supply to the hemorrhoid. And, in some embodiments, the occlusion device applies heat to the vascular supply to the hemorrhoid at a temperature ranging from about 50° C. to about 65° C for an effective time to selectively coagulate the vascular supply during the occluding while avoiding a necrosis of the rectal tissue fold.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

Example 1

Comparison with Current Methods

This example compares current methods to the therapeutic anoscope methods taught herein, described as "gentle systems". The parameters compared are invasiveness, pain, cost, and effectiveness. The methods used as a comparison to the teachings provided herein are the energy-based methods and rubber band methods currently used in the treatment of hemorrhoids. Table 1 describes the comparison.

TABLE 1

The ratings from low to high are rated by the number of "+" symbols in a category, where the fewer number of symbols indicate "low" and the higher number of symbols "high." As can be seen, the gentle systems taught herein clearly outperform the state-of-the-art systems in most every category, as well as when averaged across all categories.

|  | State-of-the-art | | | | The gentle-systems taught herein |
| --- | --- | --- | --- | --- | --- |
|  | Energy-based | Rubber banding | Staples | Doppler-suture-based | |
| Invasiveness | + | +/++ | ++++ | ++ | + |
| Pain | +/+++ | +/++ | +++ | ++/+++ | + |
| Cost | +++ | + | ++++ | ++++ | + |
| Effectiveness | + | ++ | +++/++++ | +++/++++ | +++ |
| Procedure Time | +/++ | +/++ | ++++ | ++++ | + |

Example 2

Hemorrhoidal Superior Vessels Ligation Using Bipolar RF Energy and Gentle Securing for Treatment of Internal Hemorrhoids This example was a study of the effectiveness of an embodiment that uses a bipolar RF energy application, as described herein. Twenty-two patients having stages internal hemorrhoids at stages I-IIIA were treated. Table 2 describes the stages.

TABLE 2

| Anal bleeding | Definition | Prolapse | Definition | Stage | Definition |
| --- | --- | --- | --- | --- | --- |
| Mild | Small amount of blood on paper | Mild | Reduces spontaneously | I | Bleeding only, no hemorrhoidal prolapse |
| Moderate | Moderate or more significant amount of blood on paper | Moderate early | Requires occasional or periodic manual reduction (usually during constipation) | II | Mild hemorrhoidal prolapsed with spontaneous reduction |
| Severe | Blood is dripping in toilet bowl | Moderate advanced | Requires routine manual reduction | IIa | Mild hemorrhoidal prolapsed, requiring occasional or periodic manual reduction (usually during constipation), may or may not have bleeding |
|  |  | Severe | Cannot be effectively reduced | IIIb | Moderate hemorrhoidal prolapsed, requiring routine manual reduction, may or may not have bleeding. |
|  |  |  |  | IV | Severe prolapsed, may or may not have bleeding |

Table 3 describes the distribution of conditions among the twenty-two patients.

TABLE 3

| Bleeding | Patients # (% total) | Prolapse | Patients # (% total) | Stage | Patients # (% total) |
| --- | --- | --- | --- | --- | --- |
| Mild | 4(18.2) | Mild | 10(45.5) | I | 6(27.3) |
| Moderate | 12(54.5) | Moderate early | 6(27.3) | II | 10(45.5) |
| Severe | 6(27.3) |  |  | IIIa | 6(27.3) |
|  |  |  |  | IIIb | 0(0%) |
|  |  |  |  | IV | 0(0%) |
| Total | 22(100%) |  | 16(72.3) |  | 22(100) |

The therapeutic anoscope provided RF energy across the rectal tissue under a gentle compression, as described herein, to occlude the vascular supply to the hemorrhoid in order to avoid unnecessary damage to the surrounding tissues. The anoscope has a temperature sensor and is inserted intra-anally and the horizontal tissue fold just proximal to the internal hemorrhoid is clamped. The RF energy then is delivered to the clamped tissue until the tissue temperature reaches 55-60 C. The time of RF application ranged from 7 seconds to 29.6 seconds.

All internal hemorrhoids in left lateral, right anterior, and right posterior positions were treated during one procedure. The twenty two patients (100%) were followed at 4 weeks after the procedure. Sixteen patients (73%) were available at an average 13.1 months follow-up [range: 12.7-17.1 months].

At 4 weeks follow-up, 3 patients reported 1 episode of mild anal bleeding (13.6% vs. 100% pre-operatively or 86.7% improvement in the group), 1 patient reported mild prolapse (4.5% vs. 72.3% pre-operatively or 67.8% improvement in the group). Among 3 patients who reported mild bleeding at 4 weeks follow-up, 1 patient pre-operatively had moderate bleeding and moderate prolapse, 1 patient pre-operatively had moderate bleeding and no prolapse, and 1 patient pre-operatively had severe bleeding and mild prolapse. At an average 16.7 months follow-up, two patients who had mild anal bleeding at 4 weeks follow-up reported no anal bleeding, and one patient was not available for a long-term follow-up. The patient, who reported a mild prolapse and no bleeding at 4 weeks follow-up, pre-operatively had severe bleeding and mild prolapse. This patient reported a resolution of the prolapse at 13.3 months follow-up. The information on the symptomatic patients at 4 weeks follow-up is summarized in Table 4.

At an average 13.1 months follow-up, 1 patient reported episodic mild anal bleeding (4.5% vs. 100% in the group or 95.5% improvement), which pre-operatively reported severe bleeding and mild prolapse. None of the patients reported prolapse at an average 13.1 months follow-up. All patients reported "significant improvement" in their hemorrhoidal symptoms at an average follow-up of 13.1 months. The information on the symptomatic patient at 13.3 months follow-up is summarized in Table 5.

TABLE 4

| Patient | Symptoms at 4 weeks | Pre-operative symptoms | Symptoms at an average 13.1 months follow-up |
|---|---|---|---|
| 1 | Mild anal bleeding | Moderate bleeding and moderate early prolapsed | No bleeding and no prolapsed |
| 2 | Mild anal bleeding | Moderate bleeding, no prolapsed | No bleeding and no prolapsse 3 |
| 3 | Mild anal bleeding | Severe bleeding, mild prolapsed | No bleeding and no prolapsed |
| 4 | Mild prolapsed | Mild prolapsed and severe bleeding | No bleeding and no prolapse |

TABLE 5

| Patient | Symptoms at 13.3 months follow-up | Pre-operative symptoms | Symptoms at 4 weeks follow-up |
|---|---|---|---|
| 1 | Mild bleeding and mild anal pain, persistent anal fissure | Severe bleeding, mild prolapsed, severe anal pain secondary to anal fissure | No bleeding, no prolapsed, anal pain secondary to persistent anal fissure |

The methods taught herein, as used with the bipolar RF energy for occlusion of the superior hemorrhoidal blood supply for the treatment of the early symptomatic internal hemorrhoids (stages I-III early) showed significant improvement in pre-operative bleeding and prolapse. When compared to the pre-operative symptoms, at an average 13.1 months follow-up, the mild-to-severe anal bleeding resolved in 95.5% (improved in 100%) and mild-to-early moderate hemorrhoidal prolapse resolved in 100% of the studied patients. Of 22 initially treated patients, 16 patients (73%) were available for an average 13.1 months follow-up.

Example 3

Hemorrhoidal Superior Vessels Ligation Using Gentle Securing of a Rectal Tissue Fold and Suturing for Treatment of Internal Hemorrhoids This example illustrates a suture technique. The rectal tissue is first identified and gently secured using a therapeutic anoscope as described herein. The tissue fold is the gently sutured to occlude the vascular supply to the hemorrhoid.

The suture technique includes placing two sutures, led by needles that are approximately 1.5 cm to 2.5 cm in length. The sutures are substantially parallel to each other and are passed through the lateral aspects of the tissue fold. Both needles are then pulled outside the body of the anoscope along with the attached threads. The distal ends of the sutures, after the needles are cut off, are tied to each other using conventional surgical knots to form the first set of knots. By pulling on the proximal ends of the threads, the first surgical set of knots is delivered into the body of the anoscope and then pressed against the posterior surface of the tissue fold. The second set of surgical knots is then tied between the proximal ends of two threads and, using a surgeon's finger or an instrument, is delivered into the body of the anoscope and then pushed against the anterior surface of the tissue fold.

The locking mechanism of the anoscope is then released, the gently secured tissue is released, and the anoscope is removed from the rectum. The tissue fold stays suture-fixed after the anoscope is removed. The suture assumes an oval configuration with the two sets of knots, constructs the superior hemorrhoidal blood supply, as well as constricts and fixes the redundant tissue in a gentle manner to avoid any unnecessary tissue damage to the patient.

We claim:

1. A therapeutic anoscope for treating a hemorrhoid in a subject while avoiding trauma associated with removing a rectal tissue, the anoscope comprising:

a cylindrical, or substantially cylindrical, anoscope body having a lumen, a proximal opening, a distal end configured for a first point of entry into an anus of a subject, and a side window having a shutter and pinching surfaces to form a fold in a rectal tissue orally to a hemorrhoid and gently secure the fold with a limited pressure above a dentate line in a subject; wherein, the anoscope body is configured for providing a length sufficient to position the pinching surfaces above the dentate line in the subject; and, providing a volume in the lumen sufficient for receiving the fold of the rectal tissue for an occluding of a vascular supply to the hemorrhoid;

the shutter is configured for:

opening the window to allow the rectal tissue to enter the window during a treatment of a hemorrhoid in the subject;

creating the fold in the rectal tissue orally to the hemorrhoid; and, gently securing the fold with the limited pressure above the dentate line to avoid a removal or a necrosis of the rectal tissue that creates a trauma to the subject, wherein the limited pressure ranges from 50 kPa to 1000 kPa; and, the anoscope functions to (i) provide a visualization of the rectal tissue without an image transmission through optic fibers and (ii) facilitate an ischemic regression of the hemorrhoid through the occluding subsequent to gently securing the fold to treat the hemorrhoid in a manner that provides substantially less post procedural pain to the subject than a hemorrhoid treatment procedure that does not avoid the removal or the necrosis of the rectal tissue fold.

2. The anoscope of claim 1, wherein the anoscope includes a means for securing the fold with a controlled pressure to provide a constant tissue fold configuration.

3. The anoscope of claim 2, wherein the fold is gently secured with a controlled pressure to provide a constant tissue pressure by a spring mechanism.

4. The anoscope of claim 1, wherein the volume is sufficient for a suturing to selectively ligate the vascular supply during the occluding while otherwise avoiding the removal or the necrosis of the rectal tissue fold.

5. The anoscope of claim 1, wherein the volume is sufficient for an application of heat at a temperature of about 50° C. to about 65° C. for an effective time to selectively coagulate the vascular supply during the occluding while avoiding a necrosis of the rectal tissue fold.

6. The anoscope of claim 1, wherein the volume is sufficient for an application of an RF energy to selectively coagulate the vascular supply during the occluding while avoiding a necrosis of the rectal tissue fold.

7. The anoscope of claim 1, wherein the body has a central axis, and the limited pressure is applied in the same, or substantially same, plane as a plane formed by the rectal tissue before the pinching, and at an angle ranging from about 0 degrees to about 90 degrees from the central axis.

8. The anoscope of claim 1, wherein the body is translucent or transparent.

9. The anoscope of claim 1, wherein the pinching surfaces have an arcuate shape to facilitate recruiting the rectal tissue into the lumen of the body of the anoscope.

10. The anoscope of claim 1, wherein the fold is generally secured with a controlled pressure to provide a constant tissue pressure by providing the shutter with a material having a modulus of elasticity that prevents a user from applying a pressure greater than the pressure that creates a strain of the material.

11. The anoscope of claim 1, wherein the fold is generally secured with a controlled pressure to provide a constant tissue pressure by providing the shutter with a material having a hardness that prevents a user from applying a pressure that creates a compression of the material.

12. A system for treating a hemorrhoid in a subject in a manner that creates substantially less post-procedural pain, the system comprising:
the therapeutic anoscope of claim 1; and
an occlusion device operable for a targeted application of heat, energy, or ligation to the vascular supply to the hemorrhoid, the targeted application otherwise minimizing damage to the rectal tissue.

13. A therapeutic anoscope for treating a hemorrhoid in a subject while avoiding trauma associated with removing a rectal tissue, the anoscope comprising:
an anoscope body having a lumen, a distal end configured for a first point of entry into an anus of a subject, a side window, a movable shutter and pinching surfaces to pinch rectal tissue orally to a hemorrhoid and gently secure the tissue with a limited pressure above a dentate line in a subject by limiting an amount of pressure the pinching surfaces can apply to the rectal tissue to within a range of from 50 kPa to 1000 kPa, the shutter movable from a first position to a second position to reduce a size of the window and apply the limited pressure, the shutter gently securing the tissue to avoid a removal or a necrosis of the rectal tissue that creates a trauma to the subject, the anoscope including an occluding structure to occlude a vascular supply by application of energy subsequent to the pinching of the rectal tissue by movement of the shutter to thereby occlude a vascular supply to the hemorrhoid to facilitate an ischemic regression of the hemorrhoid through the occluding to reduce the weight of the hemorrhoid and treat the hemorrhoid in a manner that provides substantially less post procedural pain to the subject than a hemorrhoid treatment procedure that does not avoid the removal or the necrosis of the rectal tissue.

14. The anoscope of claim 13, wherein the shutter provides a controlled pressure to provide a constant tissue pressure on the rectal tissue received in the window, wherein the controlled pressure includes spring regulated pressure.

15. The anoscope of claim 13, wherein energy is applied from a region of the pinching surfaces to the rectal tissue.

16. The anoscope of claim 13, wherein the pinching surfaces have an arcuate shape and include a first pinching surface on the shutter and a second pinching surface on the window.

17. The anoscope of claim 13, wherein the shutter slides in a direction substantially parallel to the longitudinal axis of the anoscope body.

18. The anoscope of claim 13, further comprising a locking mechanism to secure the shutter in the second position.

19. The anoscope of claim 13, further comprising a refraction spring to provide a tension to retract the shutter from the second position to the first position.

20. The anoscope of claim 19, further comprising a compression spring to limit the amount of pressure than can be applied by the pinching surfaces.

21. The anoscope of claim 13, wherein the anoscope includes temperature sensor.

22. The anoscope of claim 13, wherein the occluding structure is a separate structure insertable into the lumen of the anoscope.

* * * * *